US012611282B2

(12) United States Patent
Hoffman et al.

(10) Patent No.: US 12,611,282 B2
(45) Date of Patent: Apr. 28, 2026

(54) TISSUE EXPANDERS HAVING FILL PORT ASSEMBLIES AND DRAIN PORT ASSEMBLIES THAT ARE ISOLATED FROM ONE ANOTHER FOR PREVENTING CROSS-CONTAMINATION OF FLUIDS

(71) Applicant: Mentor Worldwide LLC, Irvine, CA (US)

(72) Inventors: Michael Hoffman, Hillsborough, NJ (US); Annmarie Mullen, Bridgewater, NJ (US)

(73) Assignee: Mentor Worldwide LLC, Irvine, CA (US)

( * ) Notice: Subject to any disclaimer, the term of this patent is extended or adjusted under 35 U.S.C. 154(b) by 931 days.

(21) Appl. No.: 17/865,892

(22) Filed: Jul. 15, 2022

(65) Prior Publication Data

US 2023/0057883 A1     Feb. 23, 2023

Related U.S. Application Data

(60) Provisional application No. 63/234,528, filed on Aug. 18, 2021.

(51) Int. Cl.
*A61F 2/12* (2006.01)
*A61B 90/00* (2016.01)

(52) U.S. Cl.
CPC ............... *A61B 90/02* (2016.02); *A61F 2/12* (2013.01)

(58) Field of Classification Search
CPC .......... A61B 90/02; A61B 2017/00792; A61B 2017/00796; A61B 2090/3954;

(Continued)

(56) References Cited

U.S. PATENT DOCUMENTS

| 4,398,910 A | 8/1983 | Blake et al. |
| 4,429,693 A | 2/1984 | Blake et al. |

(Continued)

FOREIGN PATENT DOCUMENTS

| GB | 2192338 | 1/1988 |

OTHER PUBLICATIONS

International Search Report issued in corresponding International Application No. PCT/IB2022/056848, mailed on Oct. 28, 2022, 5 pages.

*Primary Examiner* — Suzette J Gherbi
(74) *Attorney, Agent, or Firm* — TROUTMAN PEPPER LOCKE LLP

(57) ABSTRACT

A tissue expander includes a shell having an anterior wall with superior and inferior zones, and one or more drainage openings formed in the inferior zone. A fill port assembly is located within the superior zone, and a drain port assembly is located within the inferior zone and is in fluid communication with the one or more drainage openings. The fill port assembly is isolated from the drain port assembly that is located within the inferior zone. The drain port assembly includes a drain cover having an elongated body, a central hub, one or more fluid reservoirs between the first and second ends of the elongated body, and an outer face that surrounds the fluid reservoirs. The outer face of the drain cover is secured to an inner surface of the anterior wall and surrounds the one or more drainage openings formed in the inferior zone of the shell.

21 Claims, 30 Drawing Sheets

(58) Field of Classification Search
CPC ................ A61F 2/12; A61F 2250/0003; A61F
2250/0004; A61F 2250/0059; A61F
2250/0069; A61M 39/0208; A61M 39/02
See application file for complete search history.

(56) References Cited

U.S. PATENT DOCUMENTS

| | | | | |
|---|---|---|---|---|
| 5,630,843 | A | 5/1997 | Rosenberg | |
| 6,544,214 | B1 | 4/2003 | Utterberg | |
| 6,743,254 | B2 | 6/2004 | Guest et al. | |
| 8,425,549 | B2 * | 4/2013 | Lenker | A61B 17/1214 606/198 |
| 8,454,690 | B2 | 6/2013 | McClellan | |
| 9,351,824 | B2 | 5/2016 | Renke | |
| 9,636,210 | B2 | 5/2017 | Hristov et al. | |
| 9,700,404 | B2 | 7/2017 | Martin et al. | |
| 10,070,951 | B2 | 9/2018 | Renke | |
| 11,185,384 | B2 | 11/2021 | Feinberg et al. | |
| 2007/0233273 | A1 * | 10/2007 | Connell | A61F 2/12 623/23.72 |
| 2011/0152913 | A1 | 6/2011 | Jones et al. | |
| 2011/0153017 | A1 | 6/2011 | McClellan | |
| 2011/0160854 | A1 | 6/2011 | Berg et al. | |
| 2013/0245758 | A1 | 9/2013 | Chitre et al. | |
| 2013/0325120 | A1 | 12/2013 | Mcclellan | |
| 2014/0135924 | A1 * | 5/2014 | Renke | A61F 2/12 623/8 |
| 2014/0277440 | A1 | 9/2014 | Martin et al. | |
| 2017/0035999 | A1 * | 2/2017 | Wijay | A61B 90/02 |
| 2017/0079737 | A1 | 3/2017 | Jones et al. | |
| 2019/0000608 | A1 * | 1/2019 | Renke | B29C 41/50 |
| 2019/0247138 | A1 * | 8/2019 | Kirchhevel | A61M 39/02 |
| 2020/0129258 | A1 * | 4/2020 | Feinberg | A61M 1/60 |
| 2020/0129260 | A1 * | 4/2020 | Said | A61M 25/10181 |
| 2021/0307858 | A1 * | 10/2021 | Mcclellan | A61B 5/6847 |
| 2022/0047380 | A1 * | 2/2022 | Renke | B32B 27/08 |
| 2022/0125544 | A1 * | 4/2022 | Geiger | A61M 39/0208 |
| 2023/0126362 | A1 * | 4/2023 | Schuessler | A61F 2/12 606/192 |
| 2023/0329823 | A1 * | 10/2023 | Toro Estrella | A61B 17/3421 |
| 2024/0057889 | A1 * | 2/2024 | Ramirez | A61B 90/02 |

* cited by examiner

FIG. 13E 415       425                      435

TISSUE EXPANDERS HAVING FILL PORT ASSEMBLIES AND DRAIN PORT ASSEMBLIES THAT ARE ISOLATED FROM ONE ANOTHER FOR PREVENTING CROSS-CONTAMINATION OF FLUIDS

CROSS-REFERENCE TO RELATED APPLICATIONS

The present patent application claims benefit of U.S. Provisional Application Ser. No. 63/234,528, filed on Aug. 18, 2021, the disclosure of which is hereby incorporated by reference herein.

BACKGROUND OF THE INVENTION

Field of the Invention

The present patent application is generally related to implantable devices and is more specifically related to tissue expanders having integrated drainage and fluid delivery components.

Description of the Related Art

Tissue expanders are medical devices that are implanted beneath the skin or muscle and then gradually inflated to stretch the overlying tissue. Tissue expanders are commonly used to either create a pocket for receiving a permanent prosthesis, or to generate an increased skin surface area in anticipation of the new skin being utilized for grafting or reconstruction.

Tissue expanders are typically formed of a silicone polymer shell. After implantation, a fluid, such as saline, is periodically injected into the tissue expander to enlarge it over time. Between injections, the surrounding skin is permitted to stretch and grow to create the increased skin surface and the increased tissue pocket for receipt of a permanent implant. Typically, a tissue expander has an injection element through which fluid can be introduced into or withdrawn from the shell of the tissue expander. One such injection element is an integrated port having a septum that can be pierced with a hypodermic needle for adding or withdrawing fluid from the tissue expander. Alternatively, the injection element may be a self-sealing area on the tissue expander which allows penetration by a hypodermic needle and self-closing after the needle has been withdrawn from the expander.

Most conventional, commercially available tissue expanders have a single port that is used for inflating and deflating the shell of the tissue expander. They have no means for draining fluid (e.g., seroma) that forms around the outside of the shell of the tissue expander after implantation.

After surgery, patients typically have surgical drains placed to prevent blood and lymphatic fluid from building up under the skin, allowing for a quicker recovery. Some patients are sent home with drains that are implanted and connected to an external reservoir. Emptying these reservoirs can be traumatic because the patients must periodically measure and empty the reservoirs (e.g., every morning). Many patients loathe surgical drains and look forward to having the drains removed. In addition, surgical drains may be associated with higher risks of infection. Thus, having a means to remove bodily fluid without the need for an external drain would provide great benefits for patients.

There have been some efforts directed to integrating drains into tissue expanders. For example, U.S. Published Patent Application No. 202010129258, assigned to Mentor Worldwide LLC, the disclosure of which is hereby incorporated by reference herein, teaches a tissue expander having an integrated drain includes an outer shell having an opening and one or more drainage holes. An injection port is disposed in the opening of the shell and forms a fluid-tight seal with the shell. The injection port includes a needle guard having a needle guard base with a top surface, and a barrier membrane that overlies the top surface of the needle guard base. The barrier membrane defines an inflation chamber located between the top surface of the needle guard base and a bottom surface of the barrier membrane; and a drainage chamber overlying a top surface of the barrier membrane. The tissue expander includes one or more inflation ports that are in fluid communication with the inflation chamber for inflating and deflating the outer shell with a first fluid. A drainage conduit is in fluid communication with and extends between the drainage chamber and the one or more drainage holes for draining a second fluid from outside the shell.

U.S. Pat. No. 8,454,690 to McClellan discloses a tissue expander having an implant shell that is filled via an inflation port. The tissue expander has a pocket that extends around the implant shell. The pocket contains a drainage channel that can be used to drain fluid. A drainage port located in a superior region of the shell of the tissue expander is coupled with the drainage channel via an elongated communication channel that extends between the drainage channel and the drainage port. In McClellan, the drainage port is located in a superior region of the breast, which potentially increases the risk of infection because the superior region of the breast that is not normally exposed to drainage fluid because drains are typically placed in the inferior region of the breast.

In addition, in McClellan, the fill port and the drainage port are both located in the superior region of the breast. The proximity of the fill port and the drain port may potentially result in cross-contamination of the filling lumen and the drainage lumen since the needles are passing through the same superior breast tissue. This may lead to contamination of the interior of the tissue expander, which may culture and be released back into the breast pocket if there is inadvertent deflation and rupture of the expander. In addition, in McClellan, the communication channel is an elongated feature that runs a substantial distance between the port and the drainage delivery canal. The communication channel adds additional bulk to the expander and potentially additional mechanical failure modes, for example, when folding the expander to place the expander into the breast pocket.

In view of the above-noted problems, there is a need for improved tissue expanders having integrated fill port assemblies and drainage port assemblies that minimize the risk of infection. In addition, there is a continuing need for improved tissue expanders having integrated fill and drainage port assemblies that minimize the likelihood that the fluid used to fill a tissue expander will be mixed and/or cross-contaminate with the bodily fluids that accumulate around the shell of the tissue expander. Moreover, there remains a need for improved tissue expanders that remove seroma fluid without the need for a drain being attached 24 hours a day to a patient.

SUMMARY OF THE INVENTION

In one embodiment, a tissue expander preferably includes two separate ports, namely, a fill port assembly that is used for adding and withdrawing fluids from a shell of the tissue expander for adjusting the size of the tissue expander and a drain port assembly that is used for draining bodily fluids that accumulate around the shell of the tissue expander after the tissue expander has been implanted in a patient.

In one embodiment, the drain port assembly may include a drain port hub that is in-line with a longitudinal axis of a drain cover that is used to collect bodily fluids.

In one embodiment, the drain port assembly may include a drain port hub that is off-set from a longitudinal axis of a drain cover that is used to collect bodily fluids.

in one embodiment, the positioning of the off-set drain port hub may shift the drain port septum away from an inframammary fold to provide for improved access relative to the inframammary fold.

In one embodiment, the tissue expander may include a self-sealing membrane that partially surrounds and/or covers areas outside the drain. The self-sealing membrane may prevent deflation due to accidental puncture, and may also prevent folding of the tissue expander when it is in a deflated state, thereby minimizing the possibility that a bare shell region will be accidentally punctured by a needle if it overlaps In one embodiment, a tissue expander has a fill port assembly and a drain port assembly that is isolated from the fill port assembly. In one embodiment, the tissue expander preferably includes a shell having an anterior wall with a superior zone and an inferior zone. In one embodiment, the shell desirably has one or more drainage openings formed in the inferior zone of the anterior wall of the shell.

In one embodiment, the fill port assembly is located within the superior zone of the anterior wall of the shell. In one embodiment, the drain port assembly is located within the inferior zone of the anterior wall of the shell. The drain port assembly is preferably in fluid communication with the one or more drainage openings formed in the inferior zone of the anterior wall of the shell.

in one embodiment, the fill port assembly that is located within the superior zone of the anterior wall of the shell is isolated from the drain port assembly that is located with the inferior zone of the anterior wall of the shell, which preferably prevents mixing and/or cross-contamination of the bodily fluids in the drain port assembly with the fluid used to fill the shell.

In one embodiment, the drain port assembly preferably includes a drain cover including an elongated body having a first end and a second end. In one embodiment, the drain cover includes a hub that is located between the first and second ends of the elongated body. The drain cover preferably has a first fluid reservoir that extends from the hub to the first end of the elongated body and a second fluid reservoir that extends from the hub to the second end of the elongated body.

In one embodiment, the outer face of the drain cover preferably surrounds the first and second fluid reservoirs. In one embodiment, the outer face of the drain cover is secured to an inner surface of the anterior wall of the shell within the inferior zone of the anterior wall. In one embodiment, the outer face of the drain cover preferably surrounds the one or more drainage openings, and the first and second fluid reservoirs are aligned with the one or more drainage openings formed in the inferior zone of the anterior wall of the shell.

In one embodiment, the hub of the drain cover preferably includes an annular rim having an open outer end and an inner end that is closed by a hub end wall. In one embodiment, one or more fluid openings may be formed in the annular rim of the hub for providing fluid communication between the hub and the first and second fluid reservoirs of the drain cover.

In embodiment, the drain port assembly preferably includes a drain port needle guard that is disposed within the hub of the drain cover. The drain port needle guard desirably has an annular rim having an open outer end and an inner end that is closed by a needle guard end wall.

In one embodiment, one or more fluid openings are formed in the annular rim of the drain port needle guard, which are preferably aligned with the one or more fluid openings formed in the annular rim of the hub for providing fluid communication between the drain port needle guard and the first and second fluid reservoirs of the drain cover.

In one embodiment, a drain port septum is desirably disposed within the open outer end of the annular rim of the drain port needle guard.

In one embodiment, a drain port magnet may be disposed between the needle guard end wall and the hub end wall to aid medical personnel in locating the drain port assembly.

In one embodiment, a drain may be disposed within the first and second fluid reservoirs of the drain cover. In one embodiment, the drain includes a first drain component that is disposed within the first fluid reservoir of the drain cover, and a second drain component that disposed within the second fluid reservoir of the drain cover.

In one embodiment, the outer face of the drain cover defines a convexly curved surface.

In one embodiment, the first and second fluid reservoirs have convexly curved shapes that match the convexly curved surface of the outer face of the drain cover.

In one embodiment, the first drain component has a convexly curved shape that matches the convexly curved shape of the first fluid reservoir and the second drain component has a convexly curved shape that matches the convexly curved shape of the second fluid reservoir.

In one embodiment, a self-sealing membrane may cover the shell within the inferior zone of the anterior wall of the shell. The self-sealing membrane may be secured to an inner surface or an outer surface of the shell.

In one embodiment, the self-sealing membrane extends superiorly from the drain port assembly toward the superior zone of the anterior wall of the shell.

In one embodiment, the elongated body of the drain cover preferably has a longitudinal axis that extends from the first end to the second end of the elongated body.

In one embodiment, the hub of the drain cover is centrally located between the first and second ends of the elongated body of the drain cover and is intersected (e.g., bisected) by the longitudinal axis of the elongated body of the drain cover.

In one embodiment, the drain port assembly may include a drain cover including an elongated body having a first end, a second end, a longitudinal axis extending from the first end to the second end, and a hub located between the first and second ends of the elongated body that is off-set from the longitudinal axis of the elongated body.

In one embodiment, the drain cover preferably includes a fluid reservoir extending from the first end to the second end of the elongated body, and an outer face that surrounds the fluid reservoir.

In one embodiment, the outer face of the drain cover is preferably secured to an inner surface of the anterior wall of the shell within the inferior zone of the anterior wall.

In one embodiment, the outer face of the drain cover desirably surrounds the one or more drainage openings, and the fluid reservoir is aligned with the one or more drainage openings formed in the inferior zone of the anterior wall of the shell.

In one embodiment, the off-set hub extends superiorly from an upper edge of the elongated body of the drain cover.

In one embodiment, the hub preferably includes an annular rim having an open outer end and an inner end that is closed by a hub end wall, and one or more fluid openings formed in the annular rim of the hub for providing fluid communication between the hub and the fluid reservoir of the drain cover.

In one embodiment, the drain port assembly preferably includes a drain disposed within the fluid reservoir of the drain cover.

In one embodiment, the drain port assembly may include a drain port needle guard disposed within the hub of the drain cover, the drain port needle guard including an annular rim having an open outer end and an inner end that is closed by a needle guard end In one embodiment, one or more fluid openings may be formed in the annular rim of the drain port needle guard, which may be aligned with the one or more fluid openings formed in the annular rim of the hub for providing fluid communication between the drain port needle guard and the fluid reservoir of the drain cover.

In one embodiment, a drain port septum ay be disposed within the open outer end of the annular rim of the drain port needle guard.

In one embodiment, a drain port magnet is disposed between the needle guard end wall and the hub end wall to help medical personnel locate the drain port assembly within the shell of the tissue expander.

In one embodiment, the tissue expander may include a self-sealing membrane that covers the shell within the inferior zone of the anterior wall of the shell, In one embodiment, the self-sealing membrane preferably extends superiorly from the drain port assembly toward the superior zone of the anterior wall of the shell.

In one embodiment, a tissue expander having a fill port assembly and a drain port assembly preferably includes a shell having an anterior wall having a superior zone and an inferior zone.

In one embodiment, one or more drainage openings are formed in the inferior zone of the anterior wall of the shell.

In one embodiment, the tissue expander preferably includes a fill port assembly located within the superior zone of the anterior wall of the shell, and a drain port assembly located within the inferior zone of the anterior wall of the shell. The drain port assembly is desirably in fluid communication with the one or more drainage openings formed in the inferior zone of the anterior wall of the shell.

In one embodiment, the drain port assembly include a drain cover having an elongated body with a first end and a second end.

In one embodiment, the drain cover may have a drain port hub that is centrally located between the first and second ends of the elongated body.

In one embodiment, the drain cover desirably includes one or more fluid reservoirs that are located between the first and second ends of the elongated body.

The drain cover preferably has an outer face that surrounds the one or more fluid reservoirs.

In one embodiment, the outer face of the drain cover is preferably secured to an inner surface of the anterior wall of the shell within the inferior zone of the anterior wall.

In one embodiment, the outer face of the drain cover preferably surrounds the one or more drainage openings, whereby the one or more fluid reservoirs are aligned with the one or more drainage openings formed in the inferior zone of the anterior wall of the shell.

In one embodiment, the fill port assembly that is located within the superior zone of the anterior wall of the shell is isolated from the drain port assembly that is located within the inferior zone of the anterior wall of the shell.

In one embodiment, a self-sealing membrane may cover the shell within the inferior zone of the anterior wall of the shell.

In one embodiment, the self-sealing membrane extends superiorly from the drain port assembly toward the superior zone of the anterior wall of the shell.

In one embodiment, the elongated body of the drain cover preferably has a longitudinal axis that extends from the first end to the second end of the elongated body. In one embodiment, the drain port hub is preferably secured to an upper edge of the elongated body and is off-set from the longitudinal axis of the elongated body.

In one embodiment, a tissue expander preferably has a fill port assembly and a drain port assembly. In one embodiment, the tissue expander desirably includes a shell having an anterior wall with a superior zone and an inferior zone, and one or more drainage openings formed in the inferior zone of the anterior wall of the shell.

In one embodiment, a fill port assembly is located within the superior zone of the anterior wall of the shell, and a drain port assembly is located within the inferior zone of the anterior wall of the shell.

The drain port assembly is preferably in fluid communication with the one or more drainage openings formed in the inferior zone of the anterior wall of the shell.

In one embodiment, the fill port assembly that is located within the superior zone of the anterior wall of the shell is isolated from the drain port assembly that is located with the inferior zone of the anterior wall of the shell.

In one embodiment, the tissue expander may be implanted in breast tissue of a patient so that the fill port assembly is located in superior breast tissue, which is closer to an upper end of the patient, and the drain port assembly is located in inferior breast tissue, which is closer to a lower end of the patient.

BRIEF DESCRIPTION OF THE DRAWINGS

FIG. 110 is a left side view of the tissue expander shown in FIGS. 11A and 11B,

FIG. 13E is a cross-sectional view of the drain port assembly shown in FIG. 13B.

DETAILED DESCRIPTION OF PREFERRED EMBODIMENTS

Figure 1A:
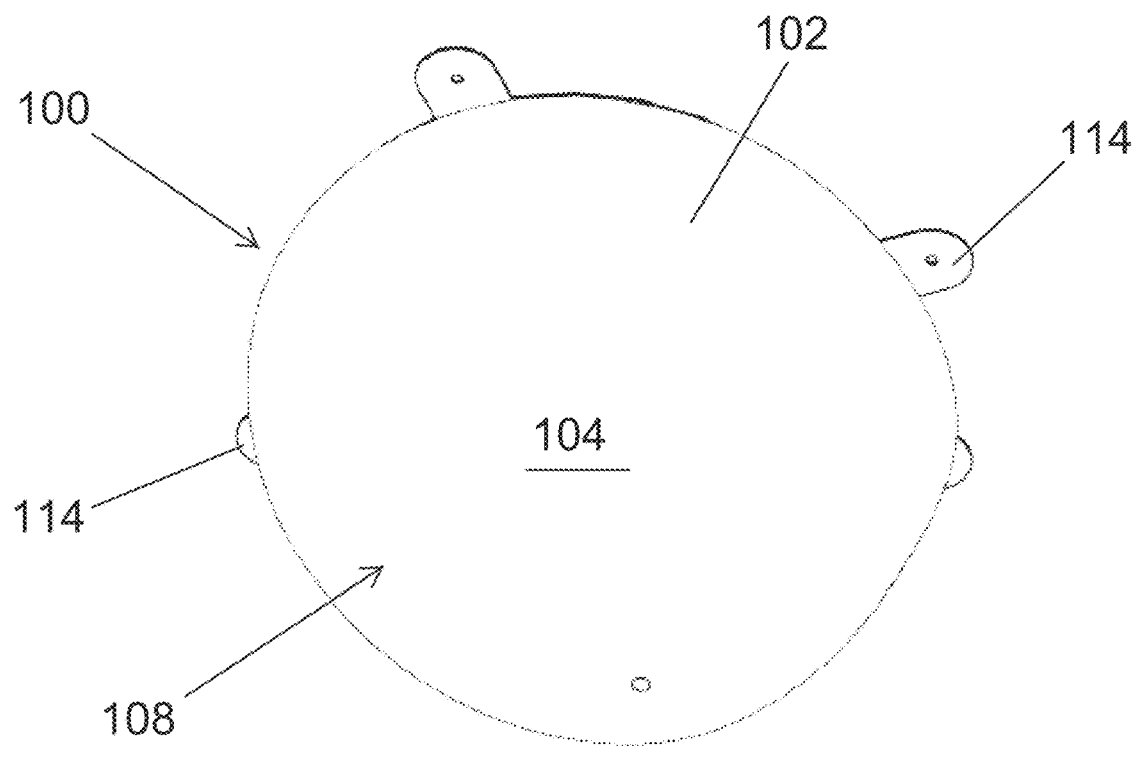
FIG. 1A is a perspective view of a topside of a tissue expander having an integrated fill port and an integrated drain port, in accordance with one embodiment of the present patent application.
Figure 1B:
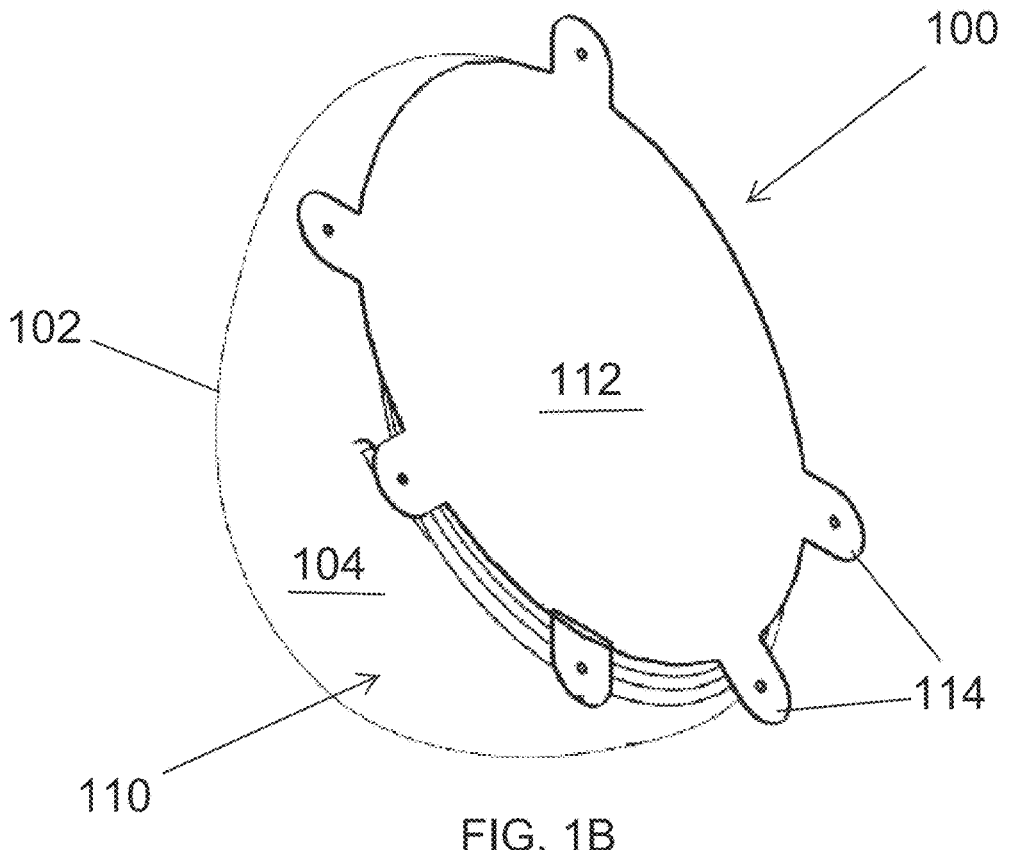
FIG. 1B is a perspective view of the underside of the tissue expander shown in FIG. 1A.
Figures 1C, 1D:
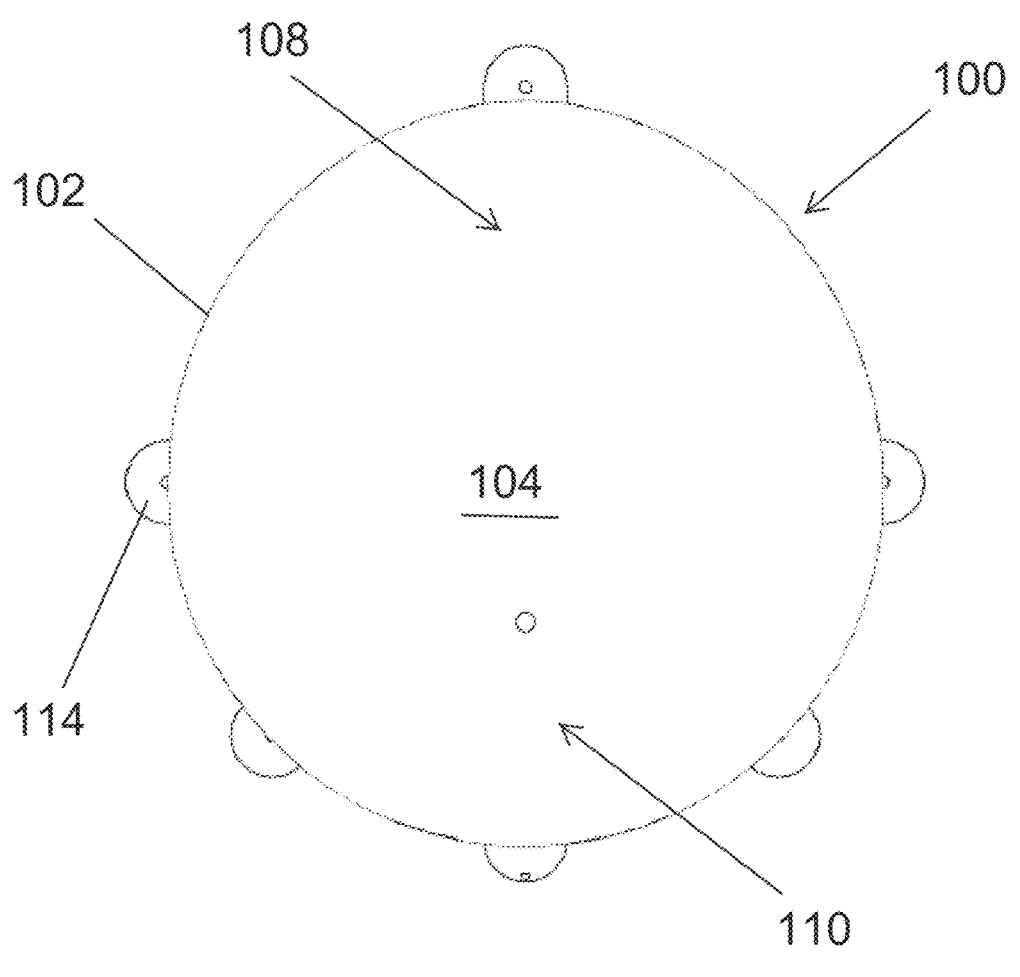
FIG. 1C is a top plan view of the tissue expander shown in FIGS. 1A and 1B.
FIG. 1D is a bottom view of the tissue expander shown in FIGS. 1A-1C.
Figure 1E:
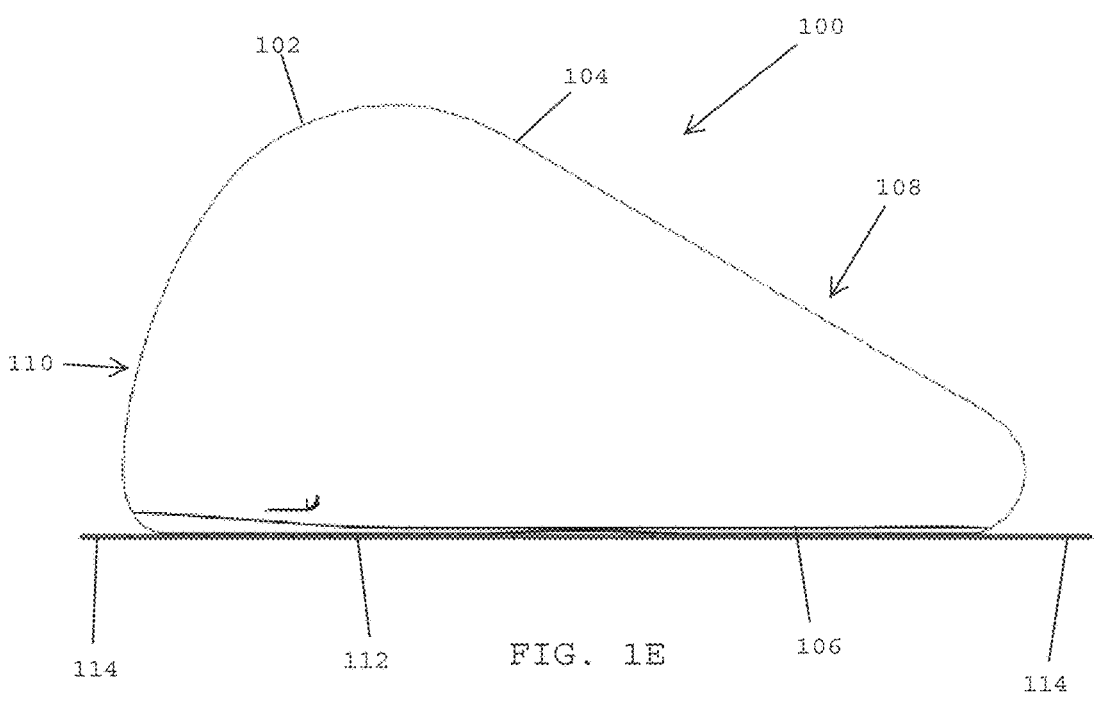
FIG. 1E is a right side view of the tissue expander shown in FIGS. 1A-1D.
Figure 1F:
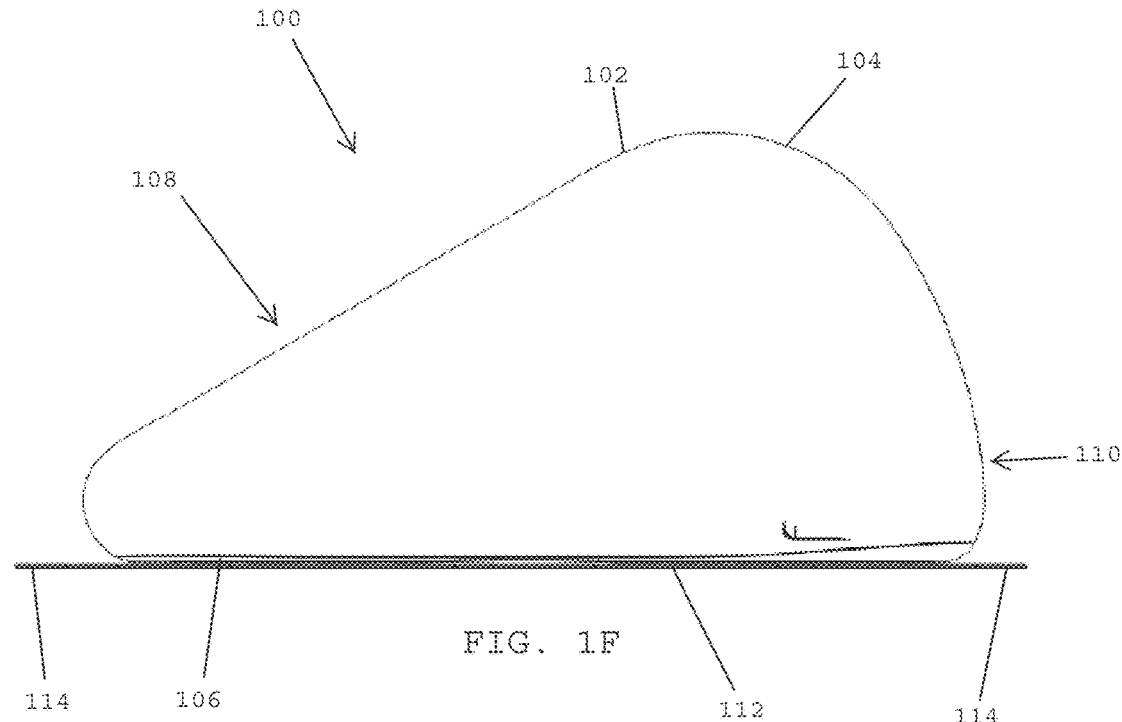
FIG. 1F is a left side view of the tissue expander shown in FIGS. 1A-1E.

Referring to FIGS. 1A-1F, in one embodiment, a tissue expander 100 preferably includes a shell 102, such as a silicone shell, having an anterior wall 104 and a posterior wall 106. In one embodiment, the anterior wall 104 of the shell 102 desirably includes a superior zone 108 and an inferior zone 110. In one embodiment, when the tissue expander 100 is implanted in a patient, the superior zone 108 of the shell 102 is preferably closer to an upper end of the patient (e.g., the head) and the inferior zone 110 of the shell 102 is preferably closer to a lower end of the patient (e.g., the feet).

In one embodiment, the tissue expander 100 preferably includes a fill port assembly (not shown) that is located within the superior zone 108 of the shell 102. In one embodiment, the fill port assembly is located inside the shell 102 and is secured to an inner surface of the shell. The fill port assembly may be used for adding fluid (e.g., saline) or removing fluid from the shell 102 to expand or reduce the outer dimension or size of the tissue expander 100.

In one embodiment, the tissue expander 100 preferably includes a drain port assembly (not shown) that is located within the inferior zone 110 of the shell 102. In one embodiment, the drain port assembly is located inside the shell 102 and is secured to an inner surface of the shell. The drain port assembly may be used for draining fluid that accumulates adjacent the inferior zone 110 of the shell 102.

In one embodiment, the tissue expander 100 desirably includes one or more drainage holes 180 (FIG. 9) that are formed in the anterior wall 104 of the shell 102. The one or more drainage holes are preferably located within the inferior zone 110 of the anterior wall 104 of the shell 102. The one or more drainage holes may be used to drain fluid (e.g., seroma fluid) that accumulates around the tissue expander 100 following surgical implantation.

In one embodiment, the tissue expander 100 preferably includes a stabilizing base 112 that is secured to the posterior wall 106 of the shell 102. In one embodiment, the stabilizing base 112 preferably includes tabs 114 that are utilized for anchoring the tissue expander 100 to tissue to prevent the tissue expander from shifting after it has been implanted in a patient.

Figure 2A:
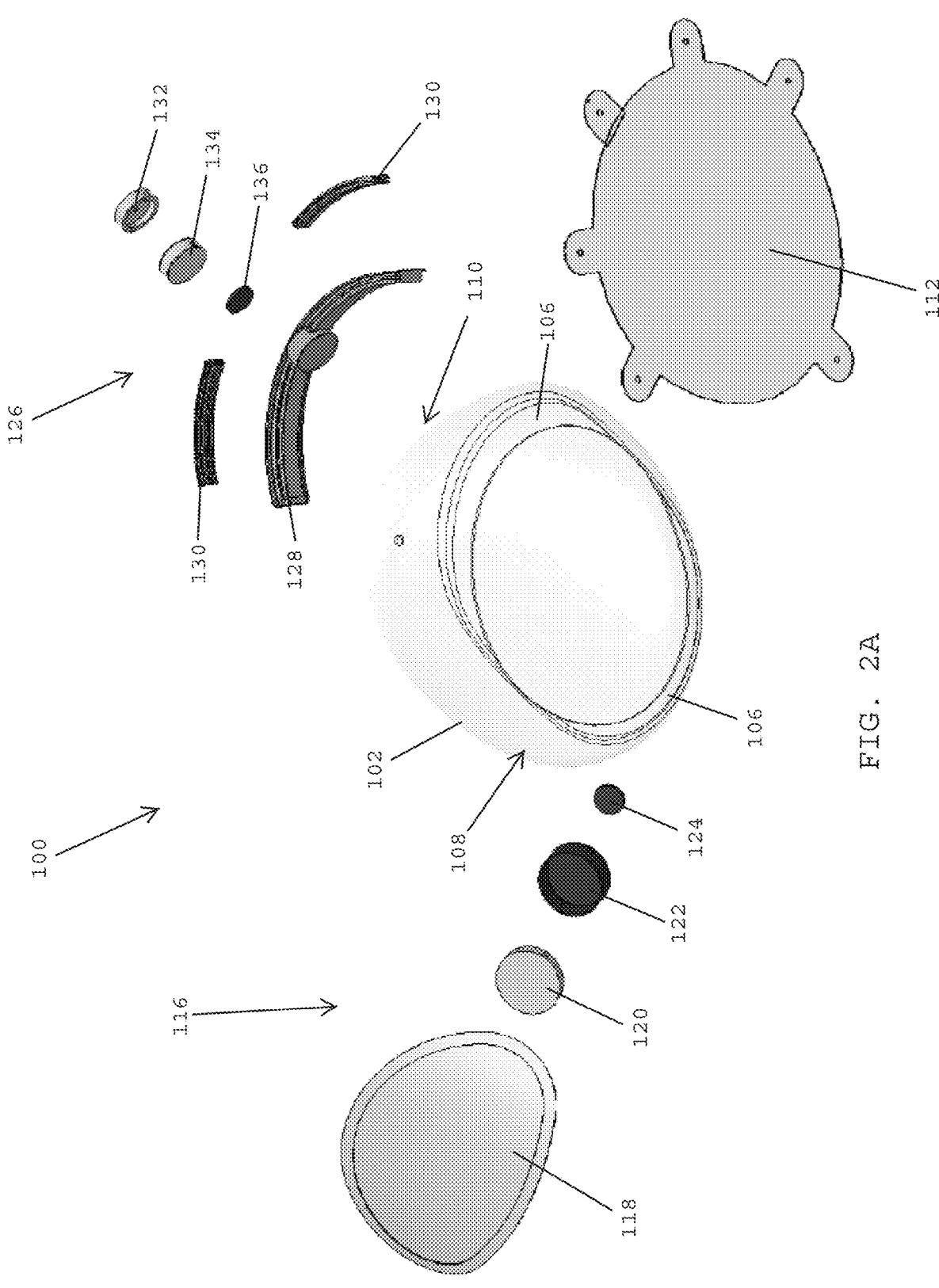
FIG. 2A is an exploded view of a tissue expander including a fill port assembly and a drain port assembly, in accordance with one embodiment of the present patent application.
Figure 2B:
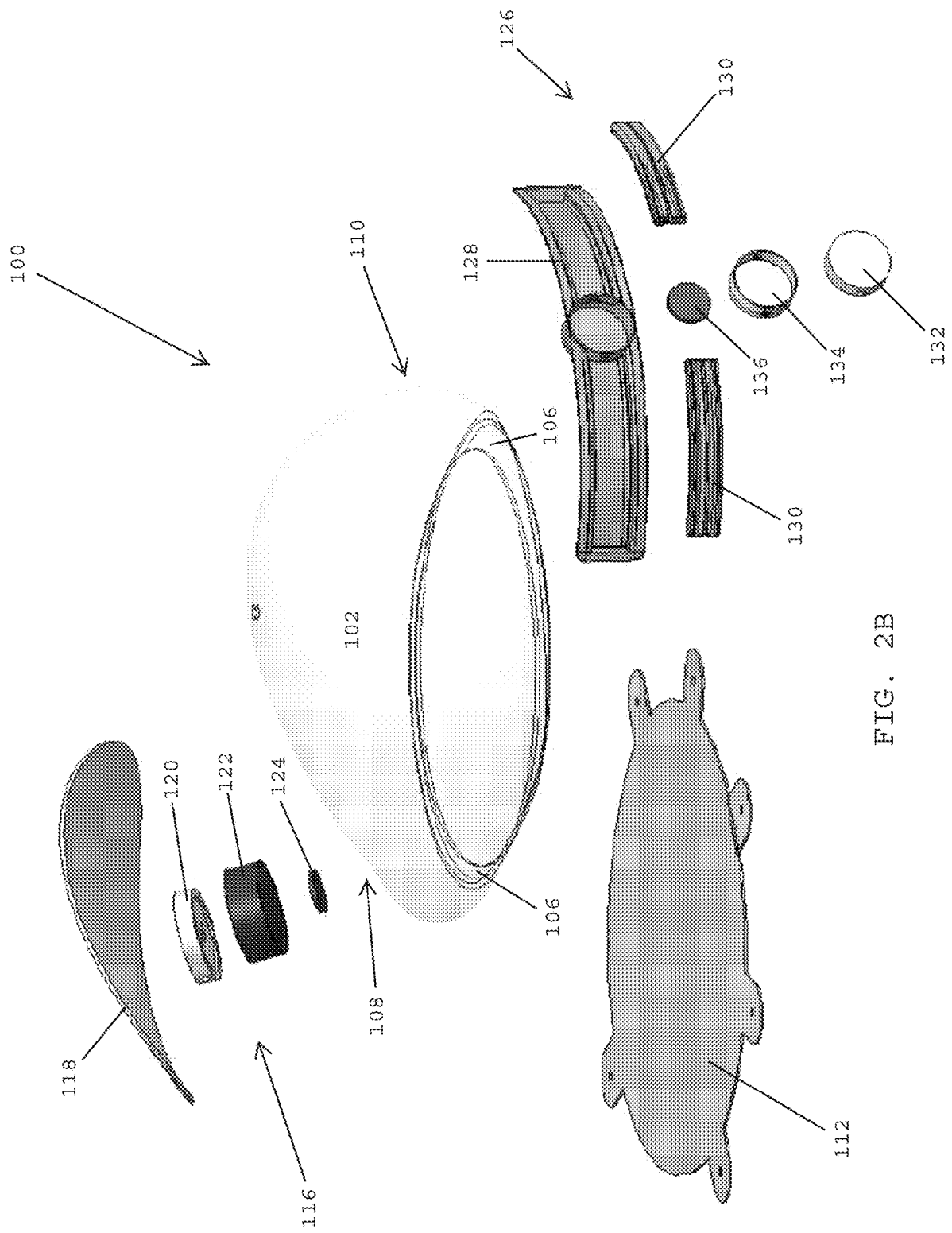
FIG. 2B is another exploded view of the tissue expander shown in FIG. 2A.
Figure 3A:
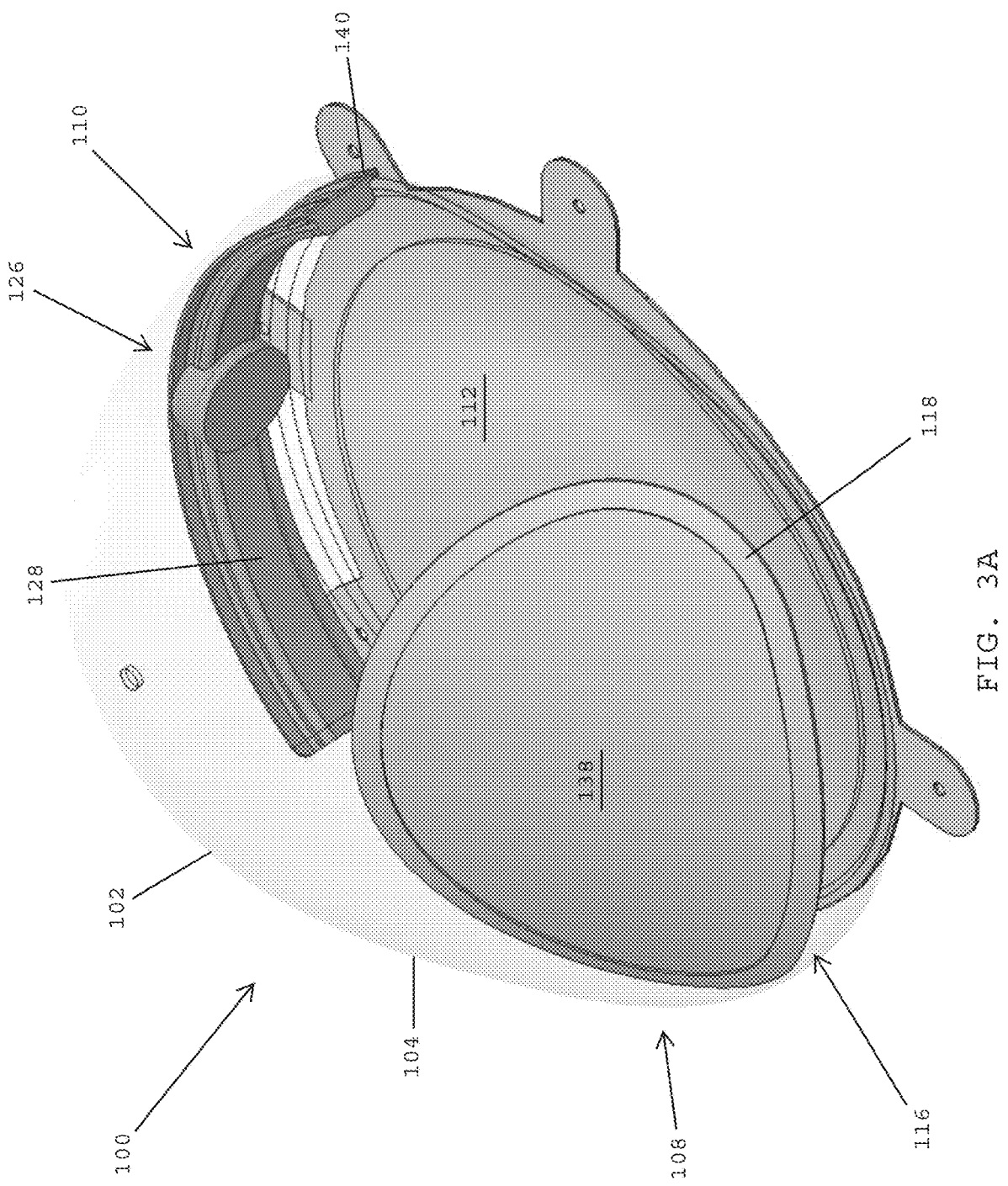
FIG. 3A is a perspective view of a tissue expander having a fill port assembly and a drain port assembly, in accordance with one embodiment of the present patent application.
Figure 3B:
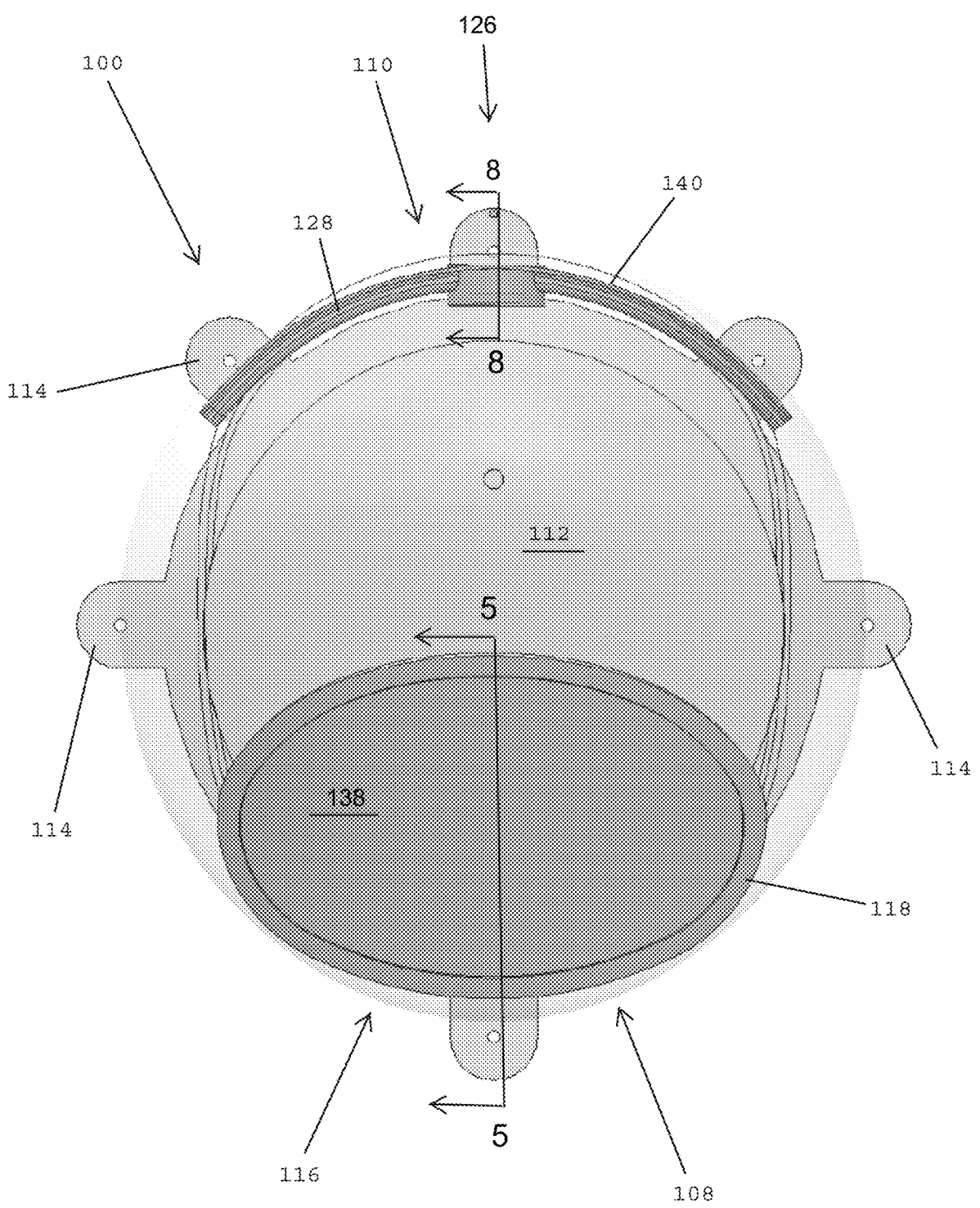
FIG. 3B is a front view of the tissue expander shown in FIG. 3A.
Figure 3C:
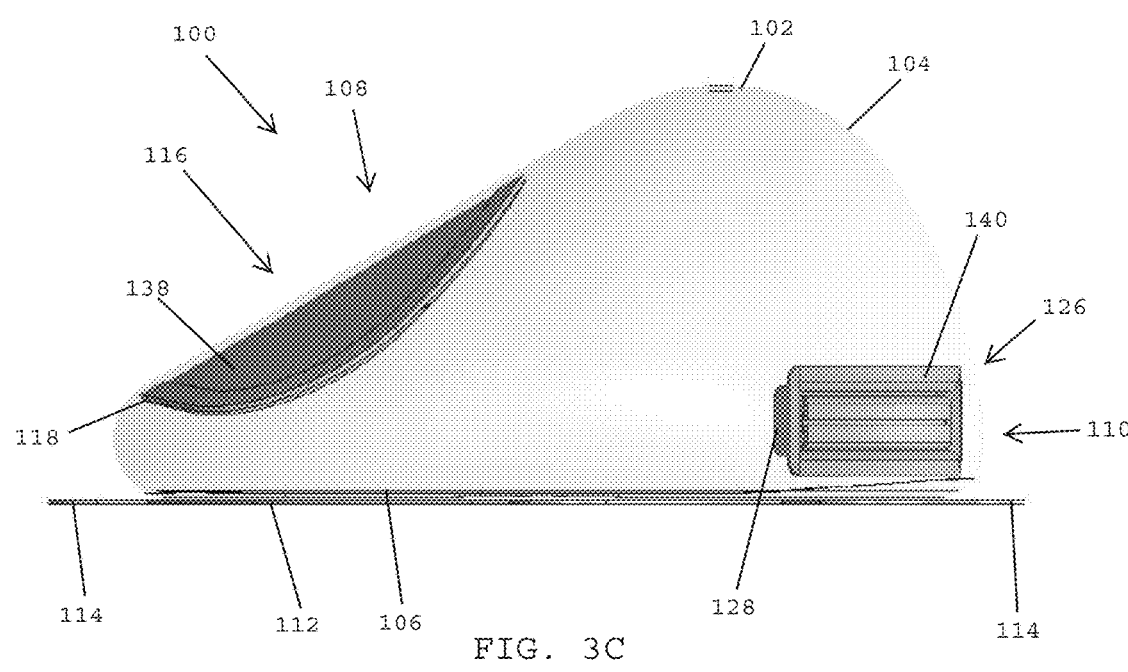
FIG. 3C is a right side view of the tissue expander shown in FIGS. 3A and 3B.
Figure 3D:
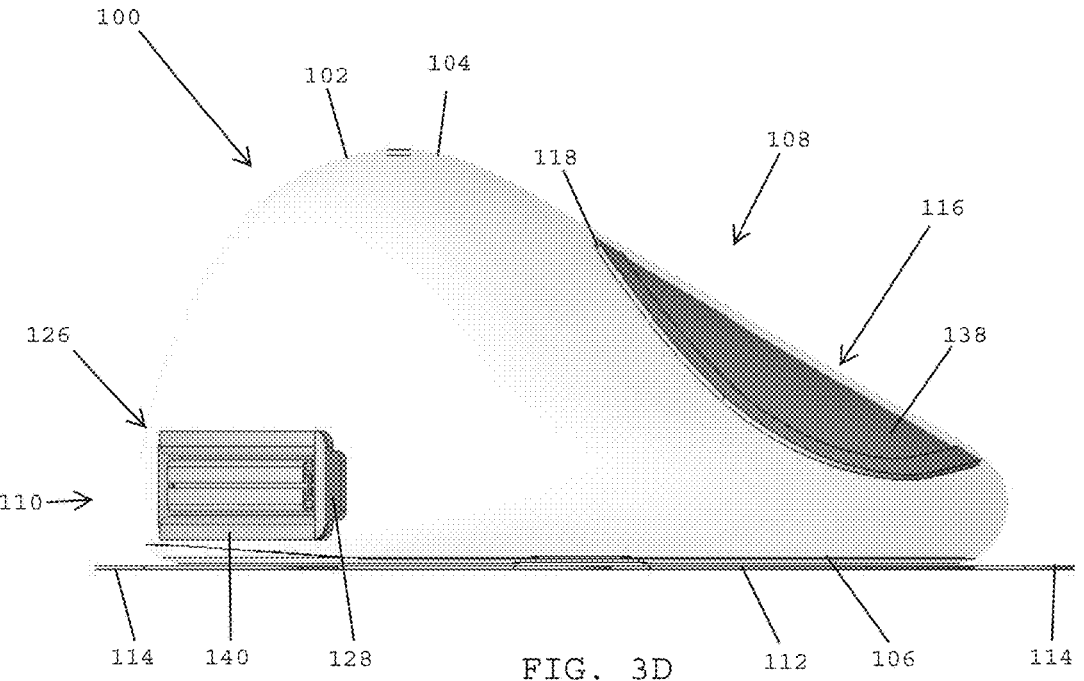
FIG. 3D is a left side view of the tissue expander shown in FIGS. 3A-30.

Referring to FIGS. 2A and 2B, in one embodiment, the tissue expander 100 preferably includes the shell 102 and the stabilizing base 112 that is adapted for being secured over the posterior wall 106 of the shell. In one embodiment, the stabilizing base 112 may close and/or seal a manufacturing opening located in the posterior wall 106 of the shell. For example, the shell 102 may be formed over a mandrel that leaves the manufacturing opening and the stabilizing base 112 covers the manufacturing opening for closing/sealing the posterior wall 106 of the shell.

In one embodiment, the tissue expander 100 preferably includes a fill port assembly 116 that may be utilized for adding fluid into and/or removing fluid from the shell 102 for adjusting the size and/or shape of the tissue expander 100. In one embodiment, the fill port assembly 116 desirably includes a self-sealing safety patch 118, a fill port septum 120, a fill port needle guard 122 that is adapted to receive the fill port septum 120, and a fill port magnet 124 that helps medical personnel to locate the fill port assembly (e.g., by using a locator magnet) after the fill port assembly has been secured inside the shell 102 of the tissue expander 100. In one embodiment, the fill port needle guard may be made of metal or may be made of polymer materials such as plastic. In one embodiment, the fill port assembly 116 is 1) located in the superior zone 108 (FIG. 1E) of the shell 102, 2) located inside the shell 102, and 3) is secured to an inner surface of the shell 102.

In one embodiment, the fill port assembly 116 is secured to the shell 102 at a location that faces toward a patient's skin surface. In one embodiment, the fill port assembly desirably includes the fill port septum that is preferably located within a central region of the fill port assembly and/or within the superior zone 108 of the anterior wall of the shell 102 of the tissue expander 100. The fill port septum is desirably self-sealing for preventing fluid leaks from the tissue expander 100 after a needle is removed from the fill port assembly 116.

In one embodiment, the tissue expander 100 preferably includes a drain port assembly 126 that is configured for draining fluid that accumulates around the shell 102 and particularly around the inferior zone 110 of the shell 102. In one embodiment, the drain port assembly 126 preferably includes a drain cover 128, a drain 130, a drain port septum 132, a drain port needle guard 134, and a drain port magnet 136. As will be described in more detail herein, the components of the drain port assembly 126 are preferably configured for being assembled and disposed inside the shell 102 of the tissue expander 100. In one embodiment, the drain port assembly 126 is 1) located in the inferior zone 110 (FIG. 1E) of the shell 102, 2) located inside the shell 102, and 3) secured to an inner surface of the shell 102 to form a water-tight seal between the drain cover and the inner surface of the shell.

In one embodiment, an appropriately sized and shaped mandrel may be used to form the shell 102 of the tissue expander 100. In one embodiment, the shell 102 may be formed using a dip molding methodology, although other methodologies may be used including spraying a mandrel with a shell forming solution or injection molding. During a dip molding method, a mandrel is dipped into silicone dispersion and then removed to allow for partial cure and solvent evaporation. The dipping step may be repeated several times. Once the shell has been formed, it is removed from the mandrel. The dip molding process results in the formation of a partial shell that has the manufacturing opening in the posterior wall 106 of the shell 102.

The seal-sealing safety patch 118 may be attached to the inner surface of the shell 102 using silicone rubber or other similar biocompatible adhesives. The completed shell can be non-filled or partially pre-filled. After implantation, the tissue expander 100 may be filled through the fill port assembly 116 with saline, gel, foam, or combinations of these materials or other suitable materials known in the art to gradually expand the tissue expander 100 to the desired dimensions. This typically takes place over the course of multiple office visits.

In one embodiment, a needle is utilized for inflating and deflating the shell 102 of the tissue expander 100. The needle preferably has a pointed tip and an opening provided at the pointed tip. In one embodiment, the pointed tip of the needle is passed through the shell 102, the seal-sealing safety patch 118, and the fill port septum 120 so that the opening at the distal end of the needle is located inside the fill port needle guard 122. Once the opening of the needle is positioned within the fill port needle guard, a fluid (e.g., saline) may be passed through the needle opening whereupon the injected fluid flows into the fill port needle guard, and through fluid openings in the outer wall of the fill port needle guard 122 for inflating the shell 102 with the fluid. To deflate the tissue expander 100, the needle may be used to remove fluid from the shell by withdrawing fluid through the fill port assembly, whereupon the fluid may be removed from the shell 102 via the needle. In one embodiment, the fluid is withdrawn through the needle using negative pressure or a vacuum.

Referring FIGS. 3A-3D, in one embodiment, the tissue expander 100 preferably includes the fill port assembly 116, which is desirably located within the superior zone 108 of the anterior wall 104 of the shell 102. In one embodiment, a major superior face 138 of the self-sealing safety patch 118 is secured to the inner surface of the shell 102, such as by using silicone rubber or other similar biocompatible adhesives.

In one embodiment, the tissue expander 100 preferably includes the drain port assembly 126, which is desirably located within the inferior zone 110 of the anterior wall 104 of the shell 102. In one embodiment, an outer face 140 of the drain cover 128 is preferably secured to the inner surface of the shell 102 to form a water-tight connection with the shell 102.

In one embodiment, the tissue expander 100 preferably includes the stabilizing base 112 that closes the manufacturing opening that is present in the posterior wall 106 of the shell 102. The stabilizing base 112 preferably includes tabs 114 that may be used to anchor the tissue expander 100 to tissue of a patient.

Figure 4:
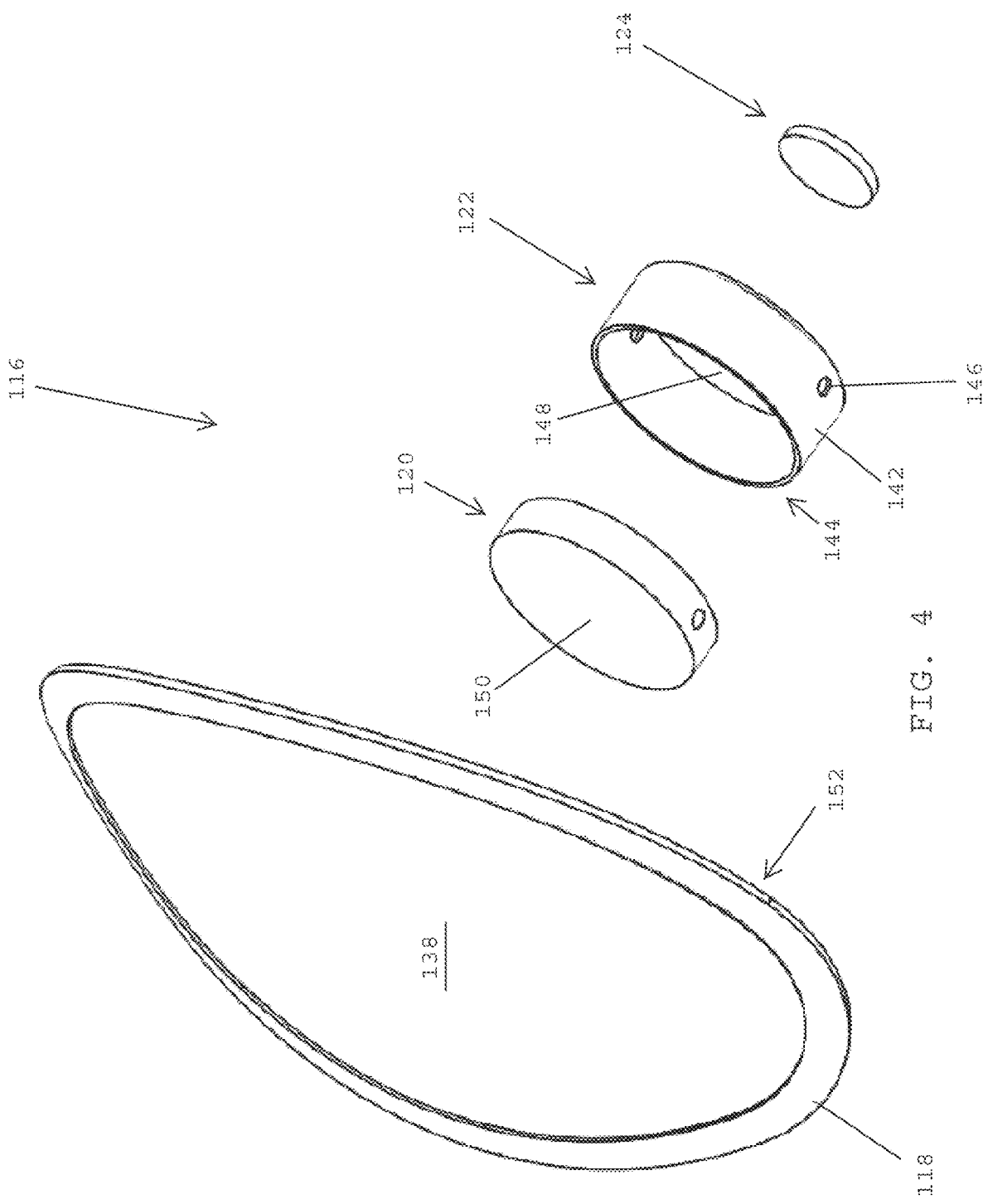
FIG. 4 is an exploded view of a fill port assembly of the tissue expander shown in FIGS. 3A-3D.

Referring to FIG. 4, in one embodiment, the fill port assembly 116 preferably includes the self-sealing safety patch 118 having the major superior surface 138 that is adapted to be abutted against and secured to the inner surface of the shell 102 (FIG. 1A). As noted above, the self-sealing safety patch 118 is preferably located within the superior zone 108 of the anterior wall 104 of the shell 102 (FIG. 1A). The self-sealing safety patch 118 preferably has an outer perimeter that surrounds the outer perimeter of the fill port needle guard 122 to provide a safety zone for preventing a leak from forming in the shell if a filling needle is inadvertently inserted into the shell at a location that is outside the perimeter of the fill port needle guard 122.

In one embodiment, the fill port assembly 116 preferably includes the fill port septum 120 that is adapted to be disposed inside the fill port needle guard 122. The fill port septum may be made of an elastomeric material such as rubber or a polymer material such as silicone. The fill port needle guard 122 preferably has a needle guard rim 142 having an open upper end 144 that is adapted to receive the fill port septum 120. The needle guard rim 142 desirably extends upwardly from the needle guard base 148. The needle guard rim 142 of the fill port needle guard 122 preferably has one or more openings 146 that enable fluid to be added into the shell 102 (FIG. 1A) of the tissue expander.

In one embodiment, the fill port magnet 124 is preferably secured to the needle guard base 148 of the fill port needle guard 122. When attempting to add or remove fluid from the shell, the fill port magnet 124 preferably helps medical personnel to locate the fill port assembly and/or the fill port septum 120.

In one embodiment, the fill port septum 120 may be bonded to the fill port needle guard 122 by using one or more uncured silicone sheets or a silicone adhesive. In one embodiment, heat may be used for curing the one or more silicone sheets or the silicone adhesive. In one embodiment, the fill port septum 120 may be bonded to the fill port needle guard 122 by mechanical means such as by using an interference fit or mating geometrical features.

Figure 5:
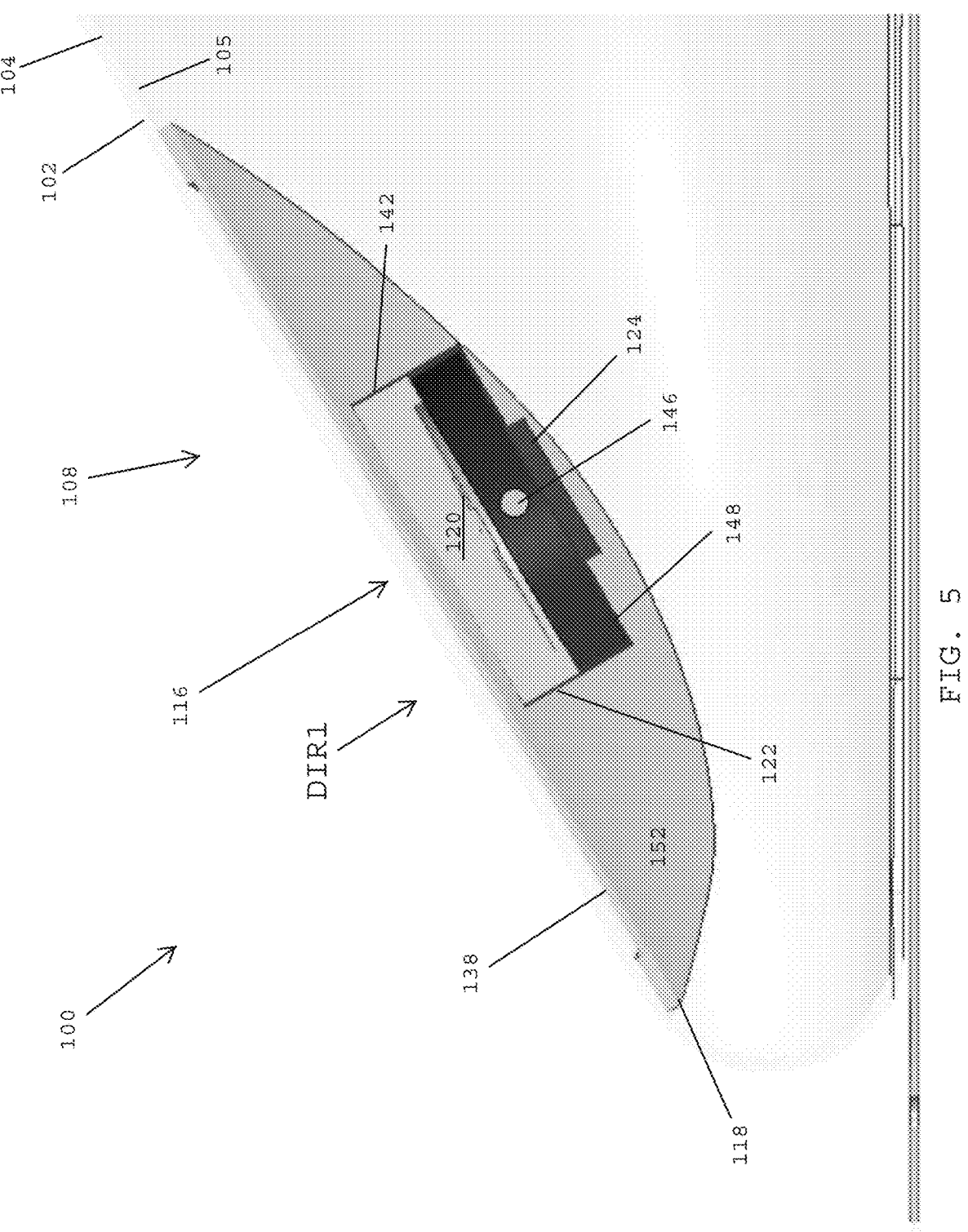
FIG. 5 is a cross-sectional view of the fill port assembly shown in FIG. 3B.

Referring to FIGS. 4 and 5, in one embodiment, after the fill port septum 120 is assembled into the open upper end 144 of the needle guard rim 142, and after the fill port magnet 124 is assembled with an underside of the needle guard base 148, a superior face 150 of the fill port septum 120 may be secured to a major inferior face 152 of the self-sealing safety patch 118.

Referring to FIG. 5, in one embodiment, the fill port assembly 116 is preferably secured to an inner surface 105 of the anterior wall 104 of the shell 102 of the tissue expander 100. In one embodiment, the fill port assembly 116 is preferably located within the superior zone 108 of the anterior wall 104 of the shell 102. In one embodiment, the superior face 138 of the self-sealing safety patch 118 is preferably secured to the inner surface 105 of the shell 102 and the superior surface 150 of the fill port septum 120 is secured to the inferior face 152 of the self-sealing safety patch 118. The self-sealing safety patch 118 preferably has an outer perimeter that is larger than the outer perimeter of the fill port needle guard 122 to provide a safety zone that surrounds the outer perimeters of the respective fill port septum 120 and fill port needle guard 122 to prevent the formation of leaks in the shell if a needle is inserted into the shell within the outer perimeter of the safety patch 118 but outside the outer perimeter of the fill port needle guard 122. The one or more openings 146 formed in the needle guard rim 142 of the fill port needle guard 122 allow fluid to be added into and/or removed from the shell 102 of the tissue expander 100. The fill port magnet 124 is preferably secured to the underside of the base 148 of the fill port needle guard 122 to help medical personnel locate the fill port assembly 116 within the shell 102 of the tissue expander 100.

In one embodiment, to add fluid to the shell 102, a distal tip of a needle (not shown) may be advanced in the direction designated DIR1 so that the distal tip passes through the anterior wall 104 of the shell 102, through the self-sealing safety patch 118, and through the fill port septum 120, whereupon the distal tip of the needle is located inside the fill port needle guard 122 for being in fluid communication with the inside of the shell 102. When the distal end of the needle has been advanced into the fill port needle guard 122, the distal tip of the needle is preferably bounded by the needle guard rim 142 and the needle guard base 148 of the fill port needle guard 122. The needle guard base 148 serves as a stop to prevent the needle from further penetration into the tissue expander 100. In one embodiment, a syringe or pump system may be activated for introducing fluid inside the shell 102 and/or removing fluid from the shell 102.

Figure 6:
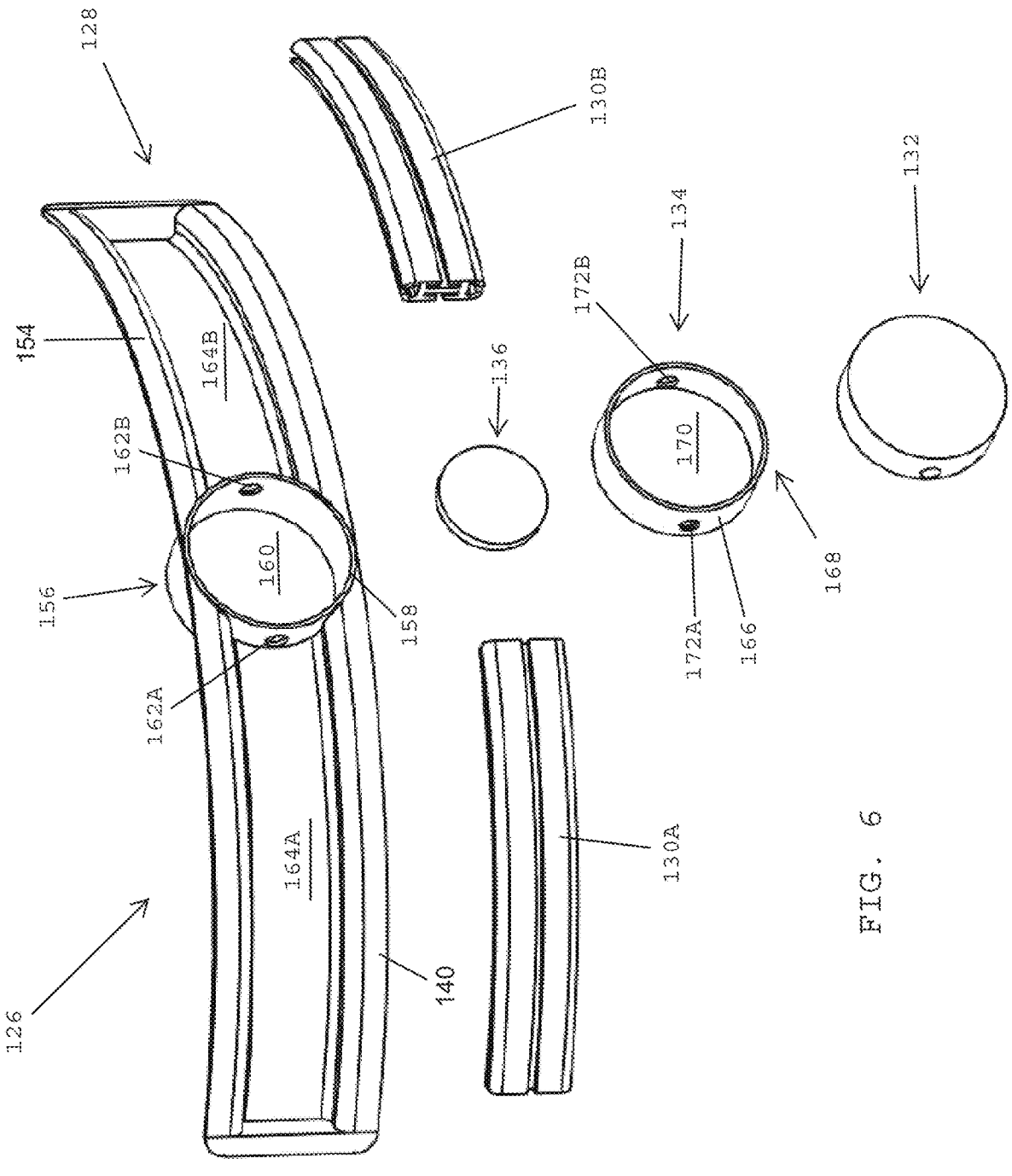
FIG. 6 is an exploded view of the drain port assembly shown in FIGS. 3A-30.
Figure 7A:
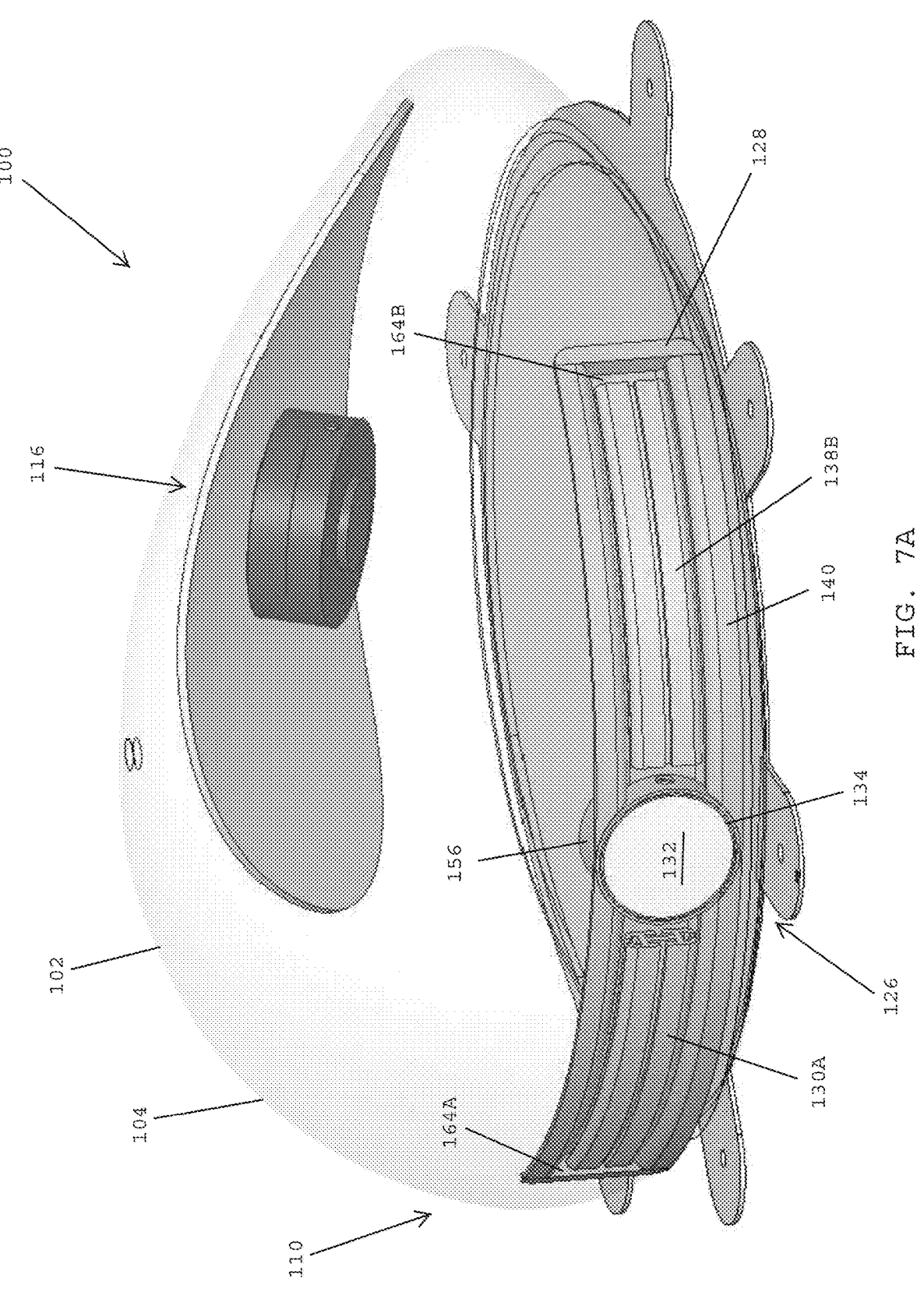
FIG. 7A is a perspective view of the drain port assembly of FIG. 6 integrated into a tissue expander, in accordance with one embodiment of the present patent application.
Figure 7B:
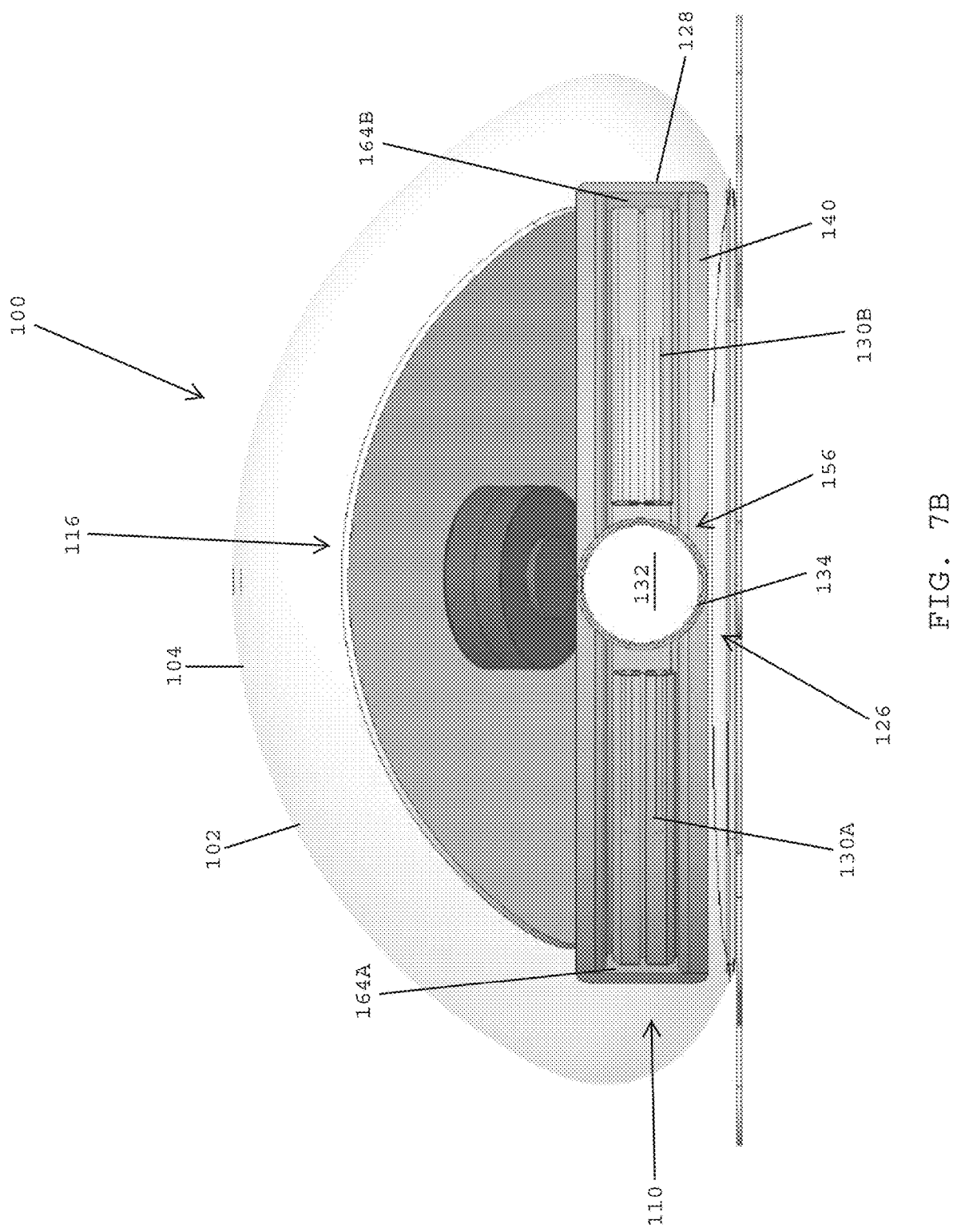
FIG. 7B is an inferior view of a tissue expander including the drain port assembly shown in FIGS. 6 and 7A.
Figure 7C:
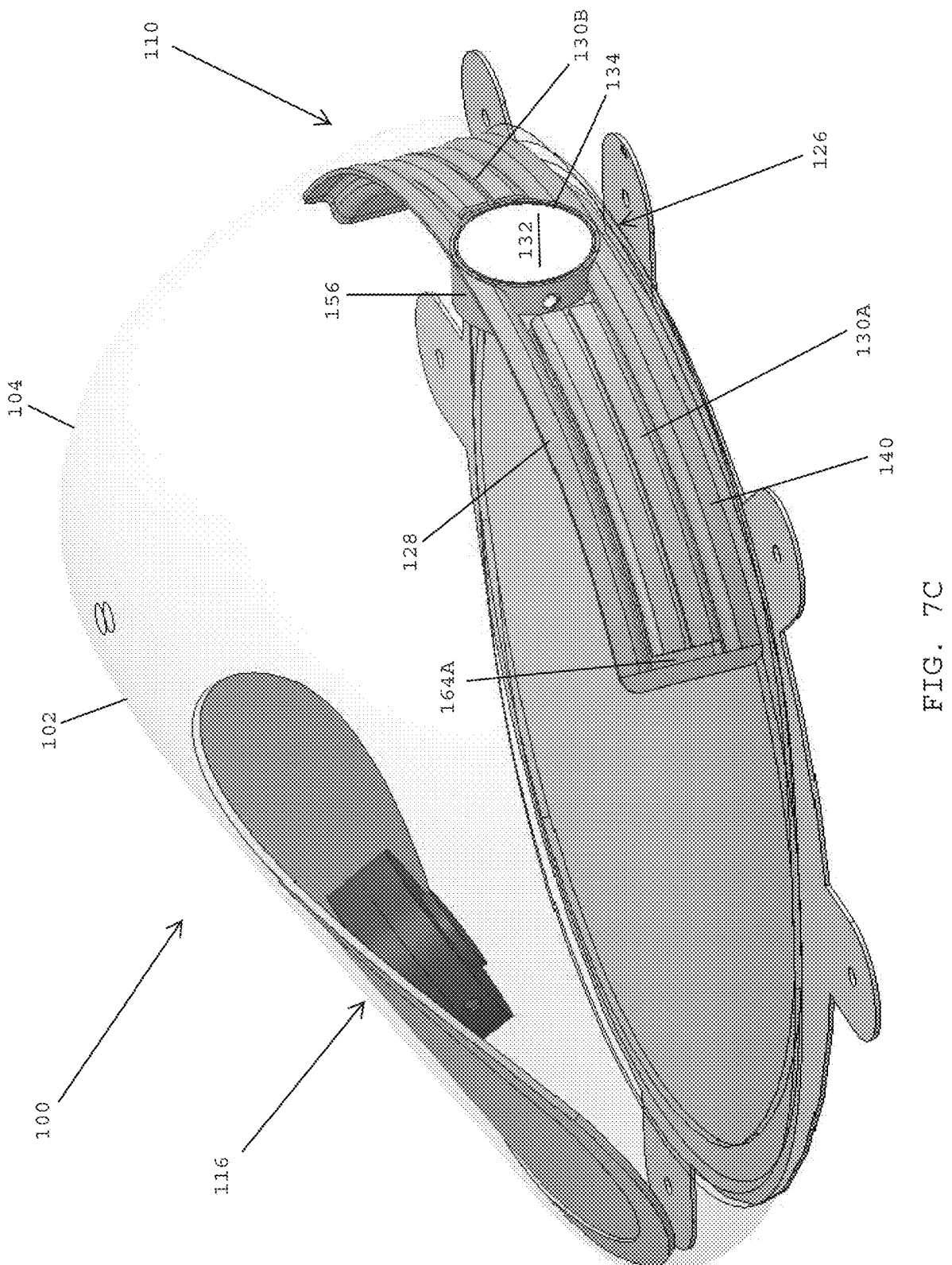
FIG. 7C is another perspective view of a tissue expander having an integrated drain port assembly, in accordance with one embodiment of the present patent application.
Figure 7D:
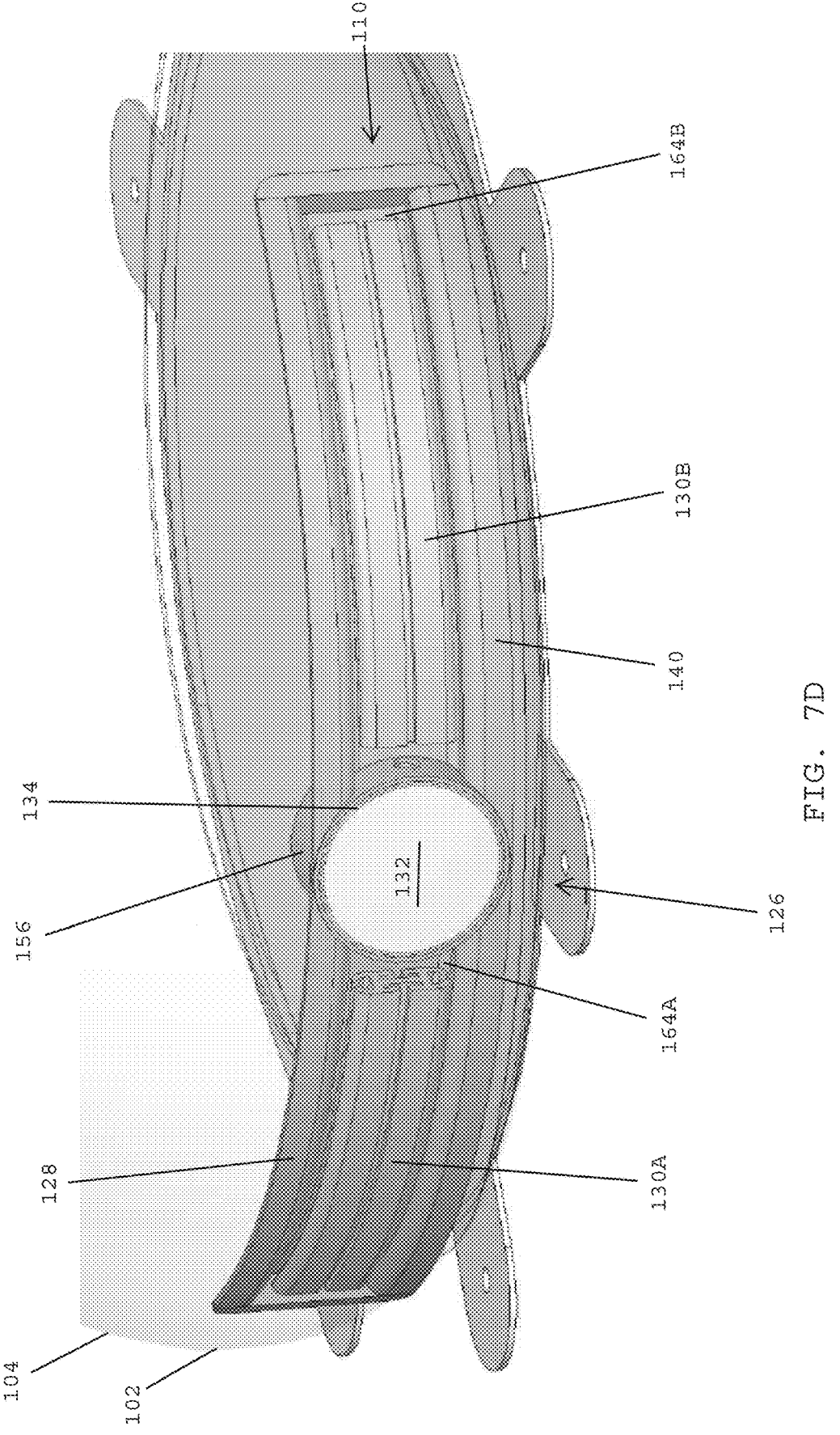
FIG. 7D is a magnified view of the drain port assembly shown in FIGS. 7A-70.

Referring to FIG. 6, in one embodiment, the drain port assembly 126 preferably includes the drain cover 128 having an outer face 140 that is adapted to be sealed against an inner surface of a shell. In one embodiment, the drain port assembly is preferably located within the inferior zone 110 of the anterior wall 104 of the shell 102 (FIG. 1A). In one embodiment, the outer face 140 of the drain cover 128 defines a convex surface that preferably conforms to (i.e., mirrors) the shape of the concave inner surface of the shell within the inferior zone of the shell, which facilitates forming a water-tight seal between the curved drain cover and the curved inner surface of the shell.

In one embodiment, the drain port assembly 126 preferably includes the drain 130 that is adapted to be assembled with the drain cover 128. In one embodiment, the drain port assembly 126 preferably includes the drain port septum 132, the drain port needle guard 134 that is adapted to seat the drain port septum 132, and the drain port magnet 136 that aids medical personnel in identifying the location of the drain port assembly 126 within the shell of the tissue expander.

In one embodiment, the drain cover 128 preferably includes an elongated body 154 having a curved shape that conforms to and/or matches the curved inner surface of the shell within the inferior zone of the anterior wall of the shell. In one embodiment, the drain cover 128 preferably includes a central hub 156. In one embodiment, the central hub 156 is located at the center of the drain cover 128. In one embodiment, the central hub 156 includes an annular rim

158 having an open outer end and an inner end that is closed by an end wall 160. The annular rim 158 or annular wall of the central hub 156 preferably includes a first fluid opening 162A and a second fluid opening 162B. In one embodiment, the drain cover 128 preferably has a first fluid reservoir 164A that is in fluid communication with the first fluid opening 162A and a second fluid reservoir 1648 that is in fluid communication with the second fluid opening 162E of the central hub 156. In one embodiment, under negative pressure, fluid that has accumulated within the first and second fluid reservoirs 164A, 164E may be drawn through the respective first and second fluid openings 162A, 162E and into the central hub 156 of the drain cover 128 for being removed from the tissue expander and/or a patient.

In one embodiment, the drain 130 preferably includes a first drain 130A that is disposed within the first fluid reservoir 164A of the drain cover 128 and a second drain 1308 that is disposed within the second fluid reservoir 1648 of the drain cover. In one embodiment, the drains 130A, 130E are desirably positioned within the respective fluid reservoirs 164A, 1648 for draining bodily fluids that have accumulated around the outer perimeter of the tissue expander. In one embodiment, the drains are desirably aligned with the drainage holes 180 (FIG. 9) formed in the shell 102 of the tissue expander 100.

In one embodiment, the drains 130A, 130B may be similar to the surgical drains disclosed in U.S. Pat. No. 4,398,910 to Blake et al., the disclosure of which is hereby incorporated by reference herein.

In one embodiment, the drain port needle guard 134 preferably includes the annular rim 166 having the open outer end 168 and the inner end that is closed by the end wall 170. In one embodiment, the annular rim 166 of the drain port needle guard 134 preferably includes first and second fluid openings 172A, 172B that are configured for allowing fluid to be drawn into the drain port needle guard 134. In one embodiment, the drain port magnet 136 is adapted to be secured to an inner face of the end wall 170 of the drain port needle guard 134. In one embodiment, the drain port septum 132 is preferably adapted to be inserted into the open outer end 168 of the annular rim 166 of the drain port needle guard 134.

In one embodiment, after the drain port septum 132, the drain port needle guard 134, and the drain port magnet 136 have been assembled, the subassembly may be inserted into the open end of the annular rim 158 of the central hub 156 of the drain cover 128. The outer face 140 of the drain cover 128 is preferably secured to the inner surface of the shell of the tissue expander to locate the drain port assembly 126 within the inferior zone of the shell of the tissue expander. The outer face of the drain cover and the inner surface of the shell preferably form a water-tight seal to isolate the bodily fluids that are collected within the drain cover from the fluids that are used to fill the shell.

In one embodiment, after the tissue expander 100 (FIG. 3A) has been implanted inside a patient, bodily fluids may accumulate around the outer perimeter of the shell of the tissue expander. The fluid typically pools within or adjacent the inferior zone of the shell of the tissue expander. In one embodiment, after passing through drain openings 180 (FIG. 9) in the shell 102, the bodily fluid is collected within the first and second drains 130A, 130B that are located within the first and second fluid reservoirs 164A, 164B of the drain cover 128. In one embodiment, to remove the bodily fluid from the tissue expander, a needle may be inserted through the inferior zone of the shell and the drain port septum 132 for locating the distal end of the needle within the drain port needle guard. When the distal end of the needle is located within the drain port needle guard, the distal end of the needle is preferably in fluid communication with the first and second drains 130A, 130E and the first and second fluid reservoirs 164A. 164B, In one embodiment, a syringe or pump system may be activated to generate a vacuum and/or negative pressure for draining the fluid that is accumulated in the first and second drains 130A, 130B and the first and second fluid reservoirs 164A, 164B of the drain cover 128. Under negative pressure and/or vacuum, the fluid that is present in the fluid reservoirs 164A, 164B is preferably drawn through the fluid openings 162A, 1628 formed in the annular rim 158 of the central hub 156, and through the fluid openings 172A, 172B formed in the annular rim 166 of the drain port needle guard 134. After the fluid has been drawn into the distal tip of the needle, the distal tip of the needle may be retracted from the drain port septum 132 of the drain port assembly 126. In one embodiment, fluid openings 162A, 162B are lamer than fluid openings 172A, 172B, and may be substantially large such that the anterior rim 158 only bounds the superior and inferior surfaces of the annular rim 166 of the drain port needle guard 134

Referring to FIG. 7A-7D, in one embodiment the drain port assembly 126 is preferably located inside the shell 102 of the tissue expander 100. In one embodiment, the drain port assembly 126 is preferably located within the inferior zone 110 of the anterior wall 104 of the shell 102. In one embodiment, the outer face 140 of the drain cover 128 preferably conforms to the shape of the inner surface of the shell 102 within the inferior zone 110 of the shell 102. The outer face 140 of the drain cover 128 is preferably secured to the inner surface of the shell 102 to form a water-tight seal therewith. The drain port septum 132 is preferably located inside the drain port needle guard 134, which, in turn, is located inside the central hub 156 of the drain cover 128. The first drain 130A is disposed within the first fluid reservoir 164A of the drain cover 128 and the second drain 130B is disposed inside the second fluid reservoir 164B of the drain cover 128.

In one embodiment, after the tissue expander has been implanted in a patient, fluid may accumulate around the inferior zone 110 of the shell 102. The fluid preferably passes through drain openings 180 (FIG. 9) formed in the shell. The drain openings are preferably in alignment with the drain cover 128 and are surrounded by the outer face of the drain cover. The fluid that passes through the drain openings 180 may be collected within the first and second drains 130A, 130B disposed within the respective first and second fluid reservoirs 164A, 164B of the drain cover 128, In one embodiment, a needle may be inserted through the anterior wall 104 of the shell 102 and advanced into the drain port septum 132 for positioning the sharpened distal tip of the needle so that it is in fluid communication with the fluid that has been collected within the first and second drains 130A, 130B. A syringe or pump system may be utilized for creating a vacuum within the drain port needle guard 134 for draining the fluid that has accumulated within the first and second reservoirs 164A, 1648 and the first and second drains 130A, 130B of the drain port assembly 126.

In one embodiment, the drain port assembly 126 is spaced away from and/or isolated from the fill port assembly 116, which preferably prevents cross-contamination of the bodily fluid that has accumulated within the drain port assembly from the fluid that is used for filling and/or inflating the tissue expander 100.

Figure 8:
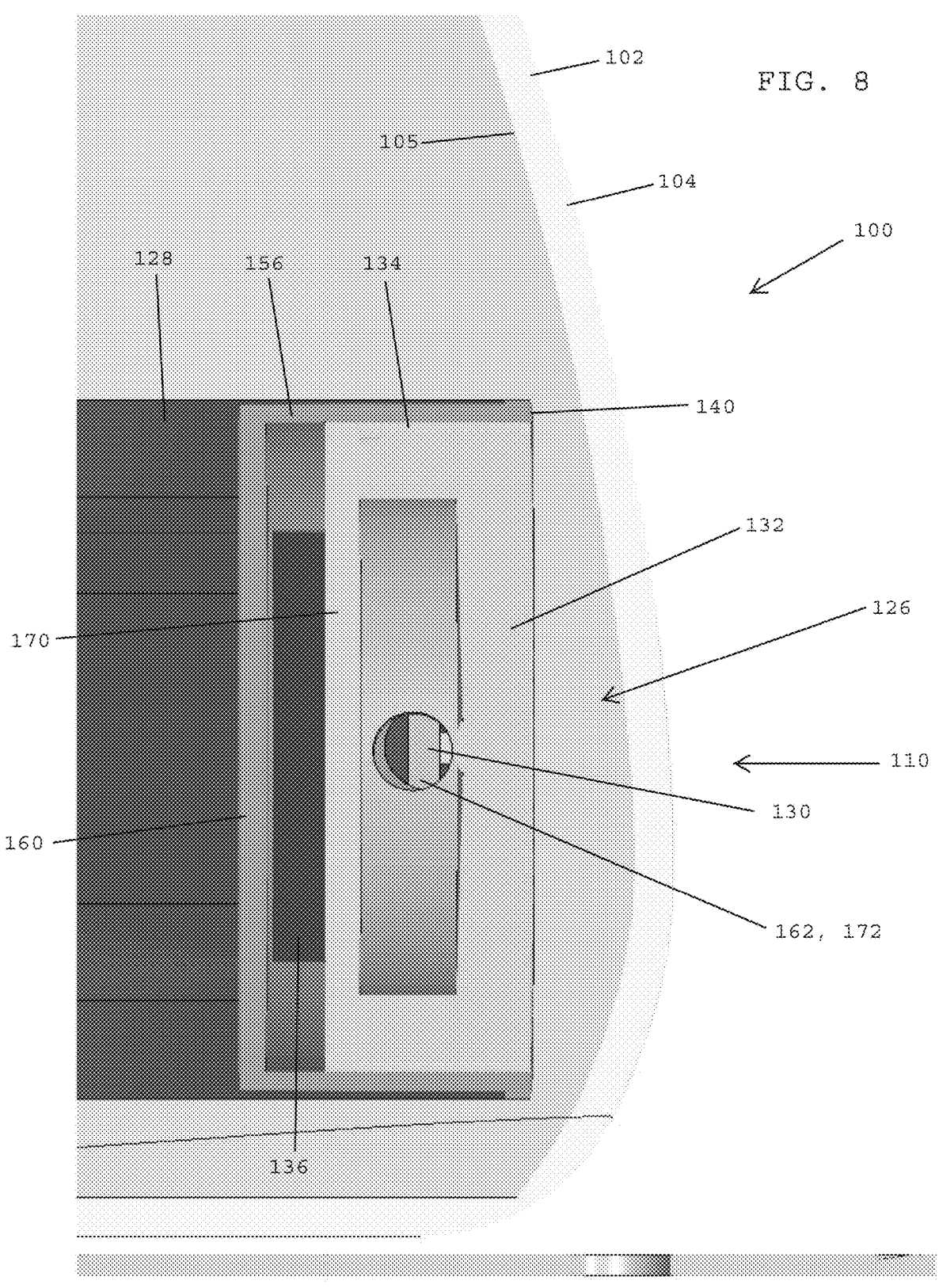
FIG. 8 is a cross-sectional view of the drain port assembly shown in FIG. 3B.

Referring to FIG. 8, in one embodiment, the drain port assembly 126 is preferably disposed inside the shell 102 of the tissue expander 100. In one embodiment, the drain port assembly 126 is preferably located within the inferior zone 110 of the anterior wall 104 of the shell 102. In one embodiment, the outer face 140 of the drain cover 128 is preferably secured to the inner surface 105 of the shell 102 to form a water-tight seal between the outer face of the drain cover 128 and the inner surface 105 of the shell 102. The presence of the water-tight seal between the drain cover 128 and the shell 102 preferably ensures that the fluid that is used to fill the shell 102 does not contact bodily fluid collected by the drain port assembly 126. In one embodiment, the drain port needle guard 134 is disposed inside the central hub 156 of the drain cover 128. The drain port magnet 136 is disposed between the bottom wall 170 of the drain port needle guard 134 and the closed wall 160 of the central hub of the drain cover 128. The drain port septum 132 is seated within the drain port needle guard 134. The fluid openings 172, 162 formed in the respective drain port needle guard 134 and the central hub 156 of the drain cover 128 provide fluid communication with the first and second drains 130A, 1308 that are disposed within the first and second fluid reservoirs 164A, 164B (FIG. 7D) of the drain cover 128.

Figure 9:
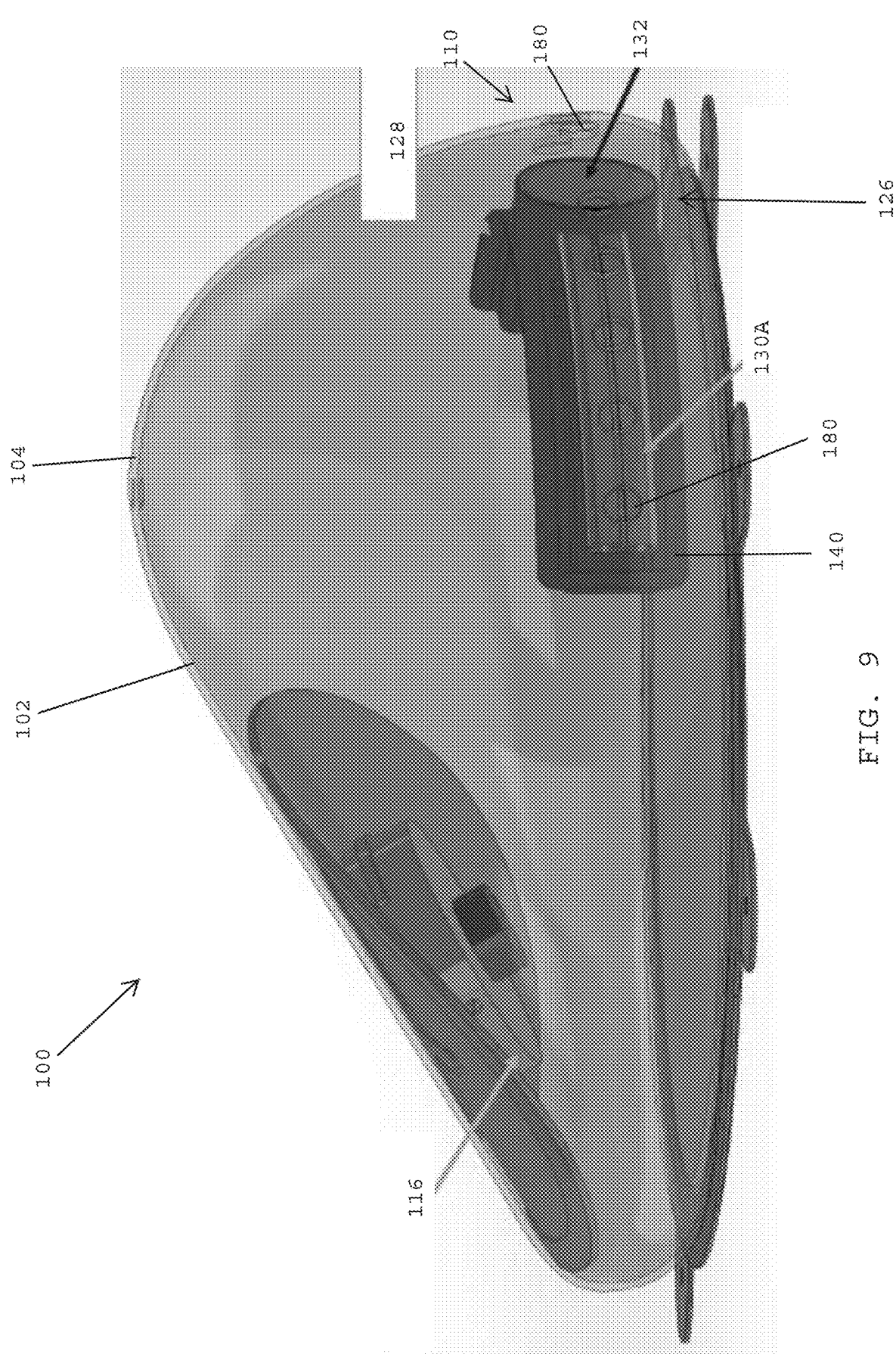
FIG. 9 is a perspective view of a tissue expander having a fill port assembly and a drain port assembly, in accordance with one embodiment of the present patent application.

Referring to FIG. 9, in one embodiment, the shell 102 of the tissue expander 100 preferably includes drainage openings 180 that are formed within the inferior zone 110 of the anterior wall 104 of the shell 102. The drainage openings 180 are preferably aligned with the first and second fluid reservoirs 164A, 164B (FIG. 6) of the drain cover 128 of the drain port assembly 126. The outer face 140 of the drain cover 128 surrounds the drainage openings 180 in the shell 102 to ensure that the bodily fluids are collected inside the drain cover 128 and do not mix with the fluid used to fill and expand the shell 102.

In one embodiment, the bodily fluid that accumulates outside the shell 102, within and/or adjacent the inferior zone 110 of the shell, preferably passes through the drainage openings 180 for being collected by the first and second drains 130A, 1308 that are disposed within the first and second fluid reservoirs of the drain cover 128. In one embodiment, a needle may be inserted into the drain port septum 132 to generate a vacuum or negative pressure for draining the fluid that has been collected inside the drains and the fluid reservoirs of the drain cover 128.

In the embodiments shown in FIGS. 2A-9, the drain cover has a central hub that is positioned "in-line" with the longitudinal axis of the drain cover, and the drain port septum, the drain port needle guard, and the drain port magnet are also positioned "in-line" with the longitudinal axis of the drain cover. In other embodiments, the location of the central hub of the drain cover, the drain port septum, the drain port needle guard, and the drain port magnet may be "off-set" from the longitudinal axis of the drain cover.

Figure 10A:
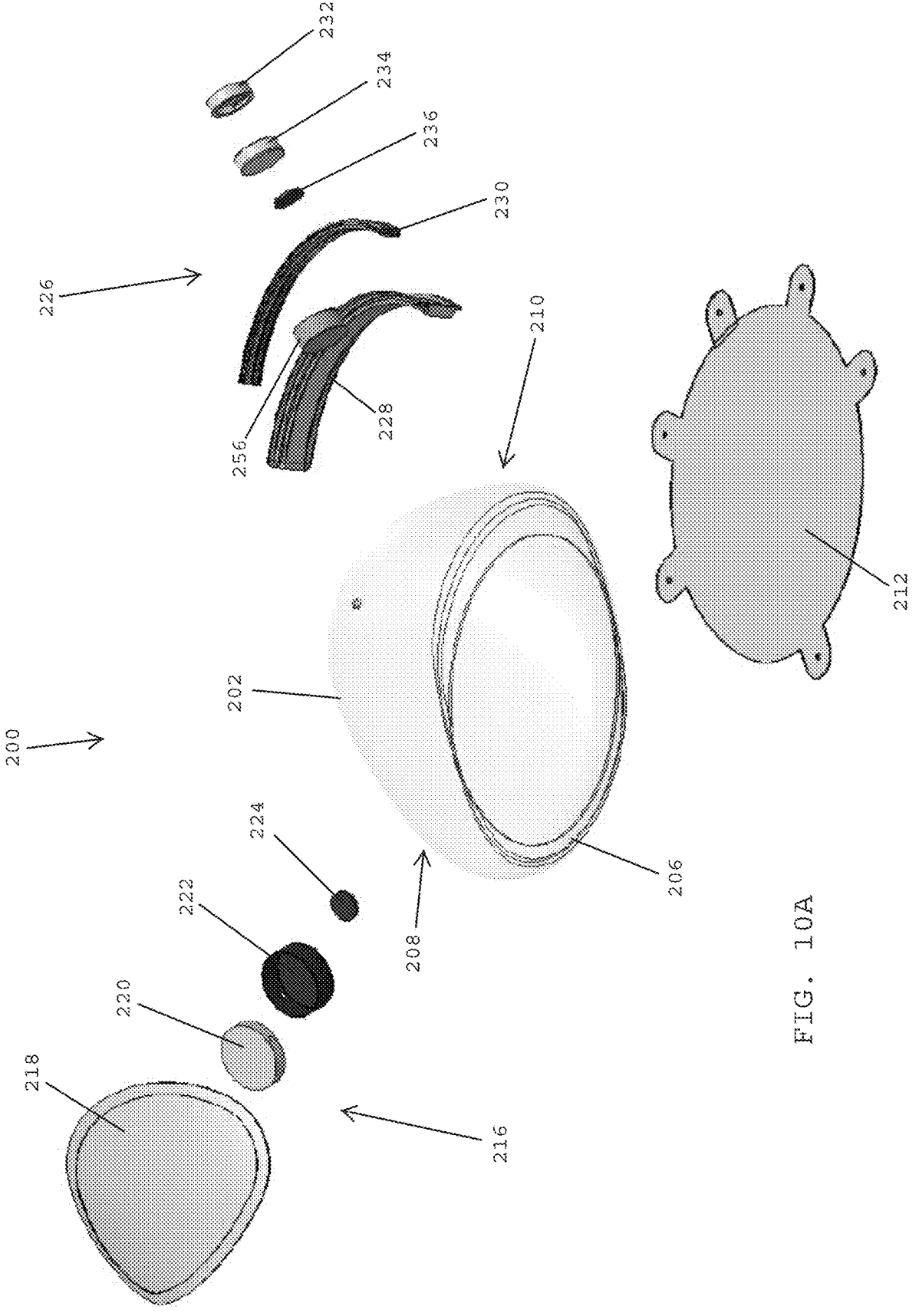
FIG. 10A is an exploded view of a tissue expander having a fill port assembly and a drain port assembly, in accordance with one embodiment of the present patent application.
Figure 10B:
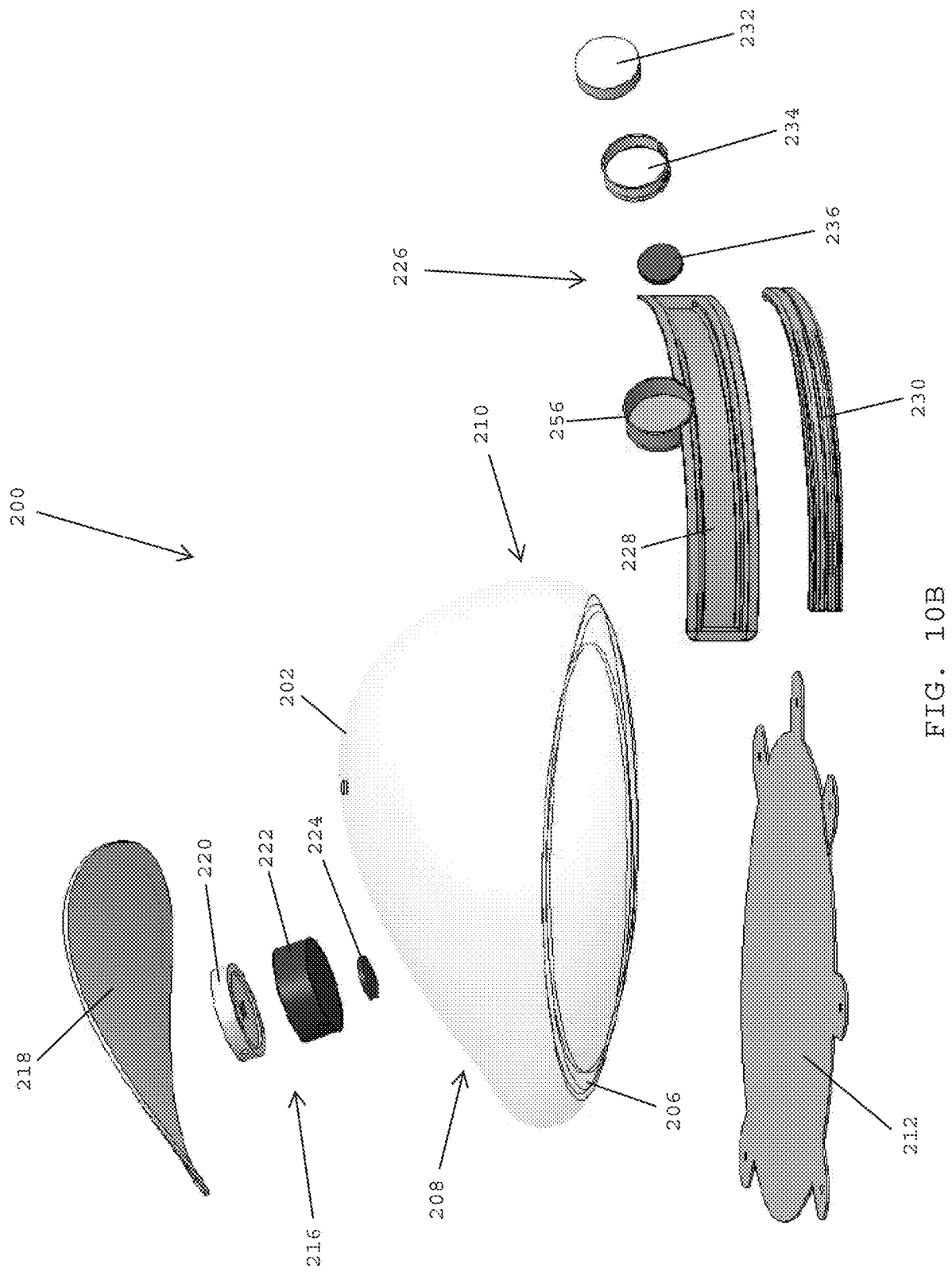
FIG. 10B is another exploded view of the tissue expander shown in FIG. 10A.

Referring to FIGS. 10A and 10B, in one embodiment, the tissue expander 200 preferably includes a shell 202 and a stabilizing base 212 that is adapted for being secured over a posterior wall 206 of the shell. In one embodiment, the stabilizing base 212 may close and/or seal a manufacturing opening located in the posterior wall 206 of the shell.

In one embodiment, the tissue expander 200 preferably includes a fill port assembly 216 that may be utilized for adding fluid (e.g., saline) into and/or removing fluid from the shell 202 for adjusting the size and/or shape of the tissue expander 200. In one embodiment, the fill port assembly 216 desirably includes a self-sealing safety patch 218, a fill port septum 220, a fill port needle guard 222 that is adapted to receive the fill port septum 220, and a fill port magnet 224 that may be utilized by medical personnel for locating the fill port assembly inside the shell 202 of the tissue expander 200. The fill port septum is desirably self-sealing for preventing the leaking of fluid from the tissue expander 200 after an injection needle is removed from the fill port assembly 216. In one embodiment, the fill port assembly 216 is 1) located in a superior zone 208 of the shell 202, 2) located inside the shell 202, and 3) is secured to an inner surface of the shell 202.

In one embodiment, the tissue expander 100 preferably includes a drain port assembly 226 that is preferably configured for draining fluid that accumulates around the outer perimeter of the tissue expander and/or the inferior zone 210 of the shell 202. in one embodiment, the drain port assembly 226 preferably includes a drain cover 228 having an off-set hub 256, a drain 230, a drain port septum 232, a drain port needle guard 234, and a drain port magnet 236. The off-set hub 256 is preferably not in alignment with the longitudinal axis of the drain cover 228. The off-set hub 256 may be located along an upper edge of the drain cover 228. In one embodiment, the drain port assembly 226 is 1) located in the inferior zone 210 of the shell 202, 2) located inside the shell 202, and 3) secured to an inner surface of the shell 202.

Figure 11A:
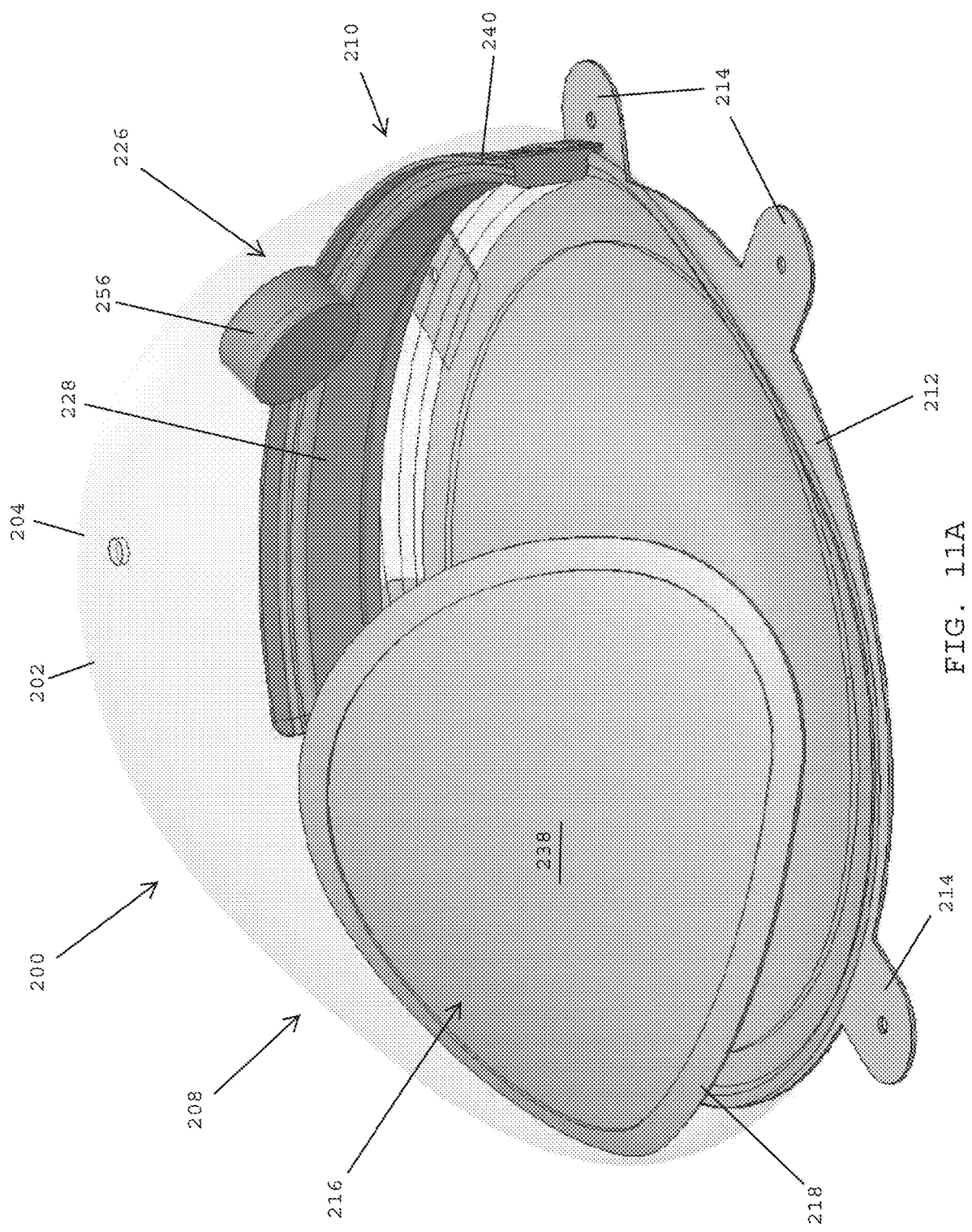
FIG. 11A is a perspective view of a tissue expander having a fill port assembly and a drain port assembly, in accordance with one embodiment of the present patent application.
Figure 11B:
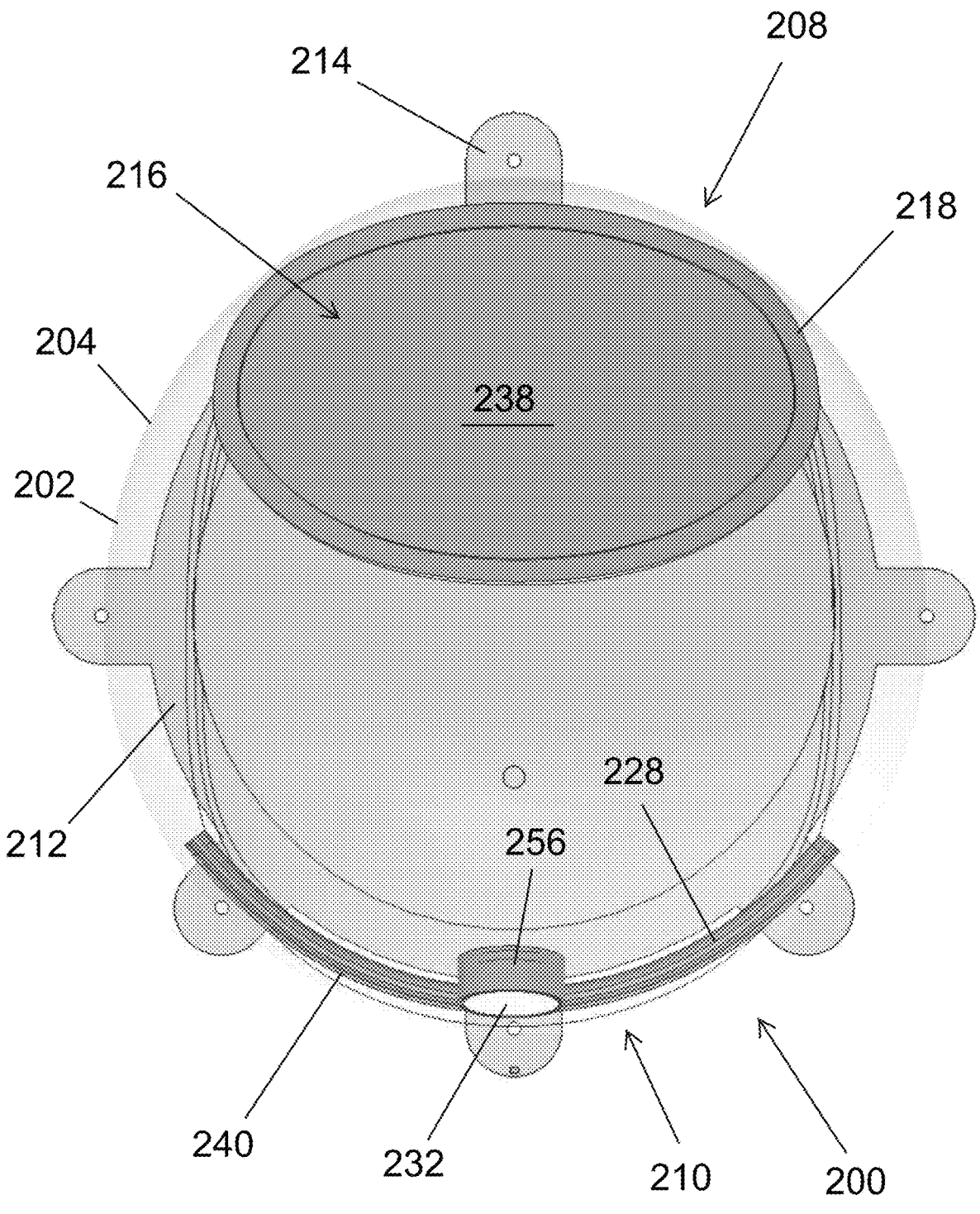
FIG. 11B is a front view of the tissue expander shown in FIG. 11A.
Figure 11C:
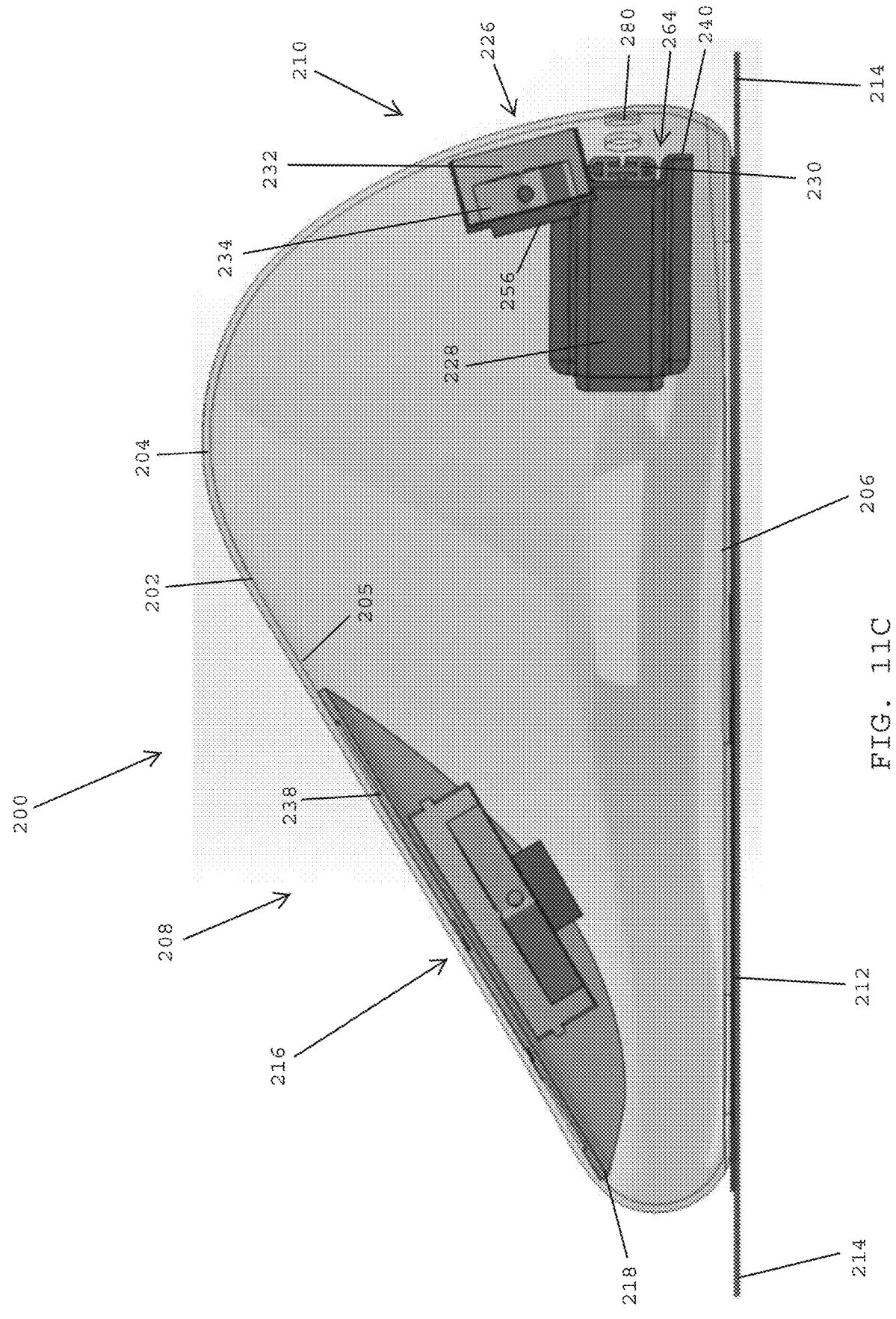

Referring FIGS. 11A-11C, in one embodiment, the tissue expander 200 preferably includes the fill port assembly 216, which is desirably located within the superior zone 208 of the anterior wall 204 of the shell 202. In one embodiment, a major superior face 238 of the self-sealing safety patch 218 is secured to the inner surface 205 of the shell 202.

In one embodiment, the tissue expander 200 preferably includes the drain port assembly 226, which is desirably located within the inferior zone 210 of the anterior wall 204 of the shell 202. In one embodiment, an outer face 240 of the drain cover 228 is preferably secured to the inner surface 205 of the shell 202 to form a water-tight seal between the drain cover and the shell 202. The water-tight seal preferably isolates the bodily fluids collected in the drain cover from the fluid that is used to fill the shell.

The drain port assembly 226 preferably includes the drain cover 228 having the off-set hub 256, the drain 230, a drain port septum 232, a drain port needle guard 234, and a drain port magnet 236. The off-set hub 256 is preferably not in alignment with the longitudinal axis of the drain cover 228.

In one embodiment, the shell 202 preferably includes drain openings 280 (FIG. 110) that extend through the shell 202 and that are aligned with the fluid reservoir 264 of the drain cover 228. The bodily fluid that passes through the drain openings 280 is directed into the drain cover for later removal via draining the fluid through the off-set hub and the drain port septum.

In one embodiment, the tissue expander 200 preferably includes the stabilizing base 212 that closes the manufacturing opening that is present in the posterior wall 206 of the shell 202. The stabilizing base 212 preferably includes tabs 214 that may be used to anchor the tissue expander 200 to tissue of a patient.

Figure 12:
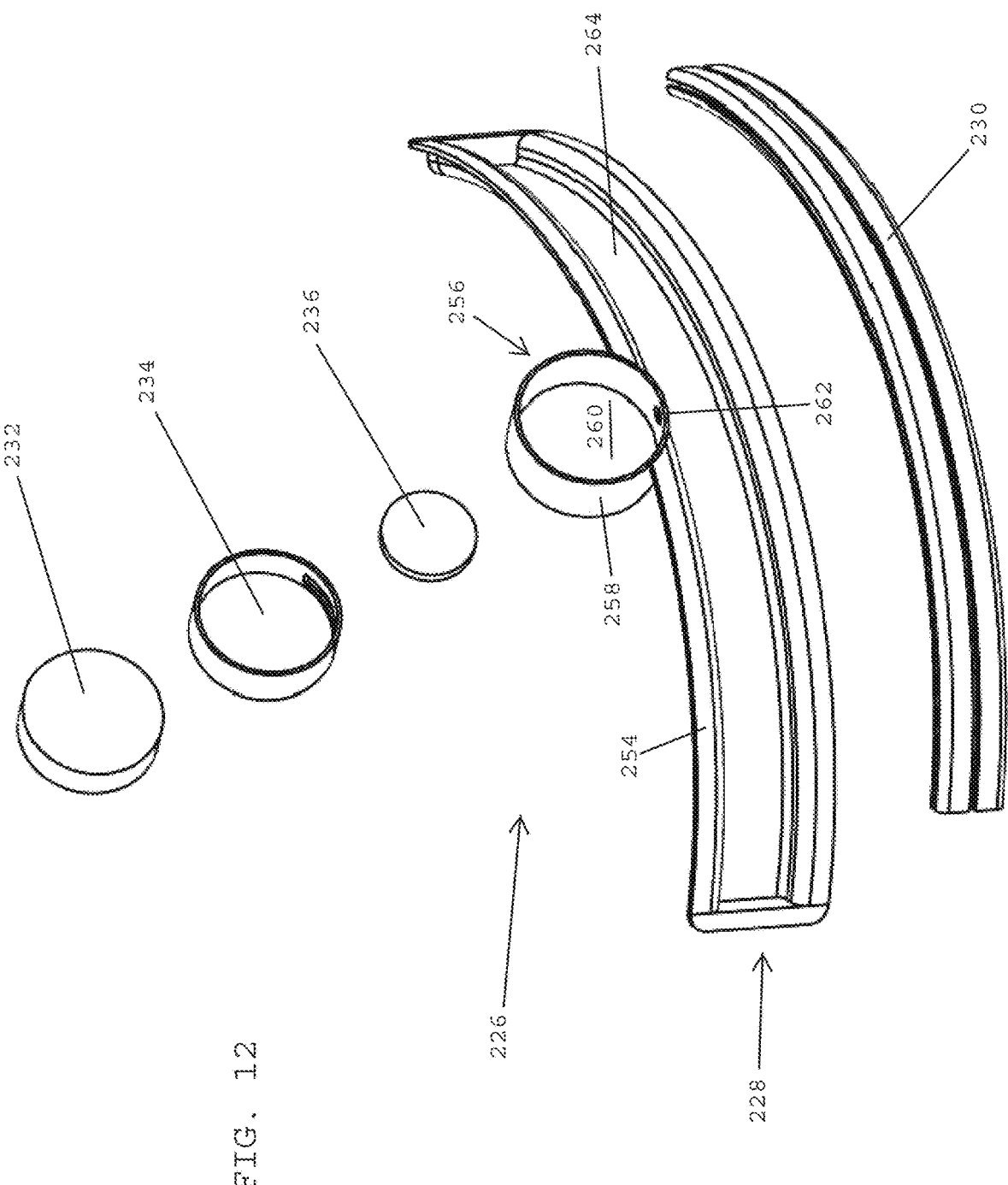
FIG. 12 is an exploded view of a drain port assembly for a tissue expander, in accordance with one embodiment of the present patent application.

Referring to FIG. 12, in one embodiment, the drain port assembly 226 preferably includes the drain cover 228 having the outer face 240 that is adapted to be sealed against an inner surface of a shell within the inferior zone 210 of the anterior wall 204 of the shell 202 (FIG. 110). In one embodiment, the outer face 240 of the drain cover 228 defines a convex curved surface that preferably conforms to (i.e., mirrors) the concave curved inner surface of the shell within the inferior zone of the shell.

In one embodiment, the drain cover 228 preferably includes an elongated body 254 having a curved shape that conforms to and/or matches the curved inner surface of the shell within the inferior zone of the anterior wall of the shell. In one embodiment, the drain cover 228 preferably includes the off-set hub 256 having an annular rim 258 having an open outer end and an inner end that is closed by an end wall 260. The annular rim 258 of the off-set hub 256 preferably includes a fluid opening 262. In one embodiment, the drain cover 228 preferably has a fluid reservoir 264 that is in fluid communication with the fluid opening 262 of the off-set hub 256. In one embodiment, under negative pressure, fluid that has accumulated within the fluid reservoir 264 of the drain cover may be drawn through the fluid opening 262 and into the off-set, hub 256 of the drain cover 228 for being removed from a patient.

In one embodiment, the drain port assembly 226 preferably includes a drain 230 that is adapted to be assembled with the drain cover 228. In one embodiment, the drain 230 is preferably disposed within the fluid reservoir 264. In one embodiment, the drain 230 is desirably positioned within the fluid reservoir 264 for draining fluid from around the perimeter of the tissue expander. In one embodiment, the drains are desirably aligned with the drainage holes 280 formed in the shell 202 of the tissue expander 200 (FIG. 11C).

In one embodiment, the drain 230 may be similar to the surgical drains disclosed in U.S. Pat. No. 4,398,910 to Blake et al., the disclosure of which is hereby incorporated by reference herein.

In one embodiment, the drain port assembly 226 preferably includes the drain port septum 232, the drain port needle guard 234 that is adapted to seat the drain port septum 232, and the drain port magnet 236 that aids medical personnel in identifying the location of the drain port assembly 226 within the shell of the tissue expander.

Referring to FIG. 13A-13D, in one embodiment the drain port assembly 226 is preferably located inside the shell 202 of the tissue expander 200. In one embodiment, the drain port assembly 226 is preferably located within the inferior zone 210 of the anterior wall 204 of the shell 202. In one embodiment, the outer face 240 of the drain cover 228 preferably conforms to the shape of the inner surface of the shell 202 within the inferior zone 210 of the shell 202. The outer face 240 of the drain 228 is preferably secured to the inner surface of the shell 202 to form a water-tight seal with the shell.

The off-set hub 256 of the drain cover 228 is adapted to receive the drain cover septum 232, the drain cover needle guard 234 (FIG. 12) and the drain port magnet 236 (FIG. 12). The hub 256 is off-set from the longitudinal axis $A_1$ (FIG. 13B) of the elongated body 254 of the drain cover 228. In one embodiment, the off-set hub 256 may be located at an upper edge of the elongated body 254 of the drain cover 228.

The drain port septum 232 is preferably located inside the drain port needle guard 234 (FIG. 12), which, in turn, is located inside the off-set hub 256 of the drain cover 228. The drain 230 is disposed within the fluid reservoir 264 of the drain cover 228.

In one embodiment, after the tissue expander has been implanted in a patient, fluid may accumulate around the inferior zone 210 of the shell 202. The fluid preferably passes through drain openings 280 (FIG. 11C) formed in the shell that are in alignment with the drain cover 228. The fluid that passes through the drain openings 280 may be collected within the drain 230 disposed inside the fluid reservoir 264 of the drain cover 228. In one embodiment, a needle may be inserted through the anterior wall 204 of the shell 202 and advanced into the drain port septum 232 for positioning the distal tip of the needle inside the drain port needle guard 234 so that the opening of the needle is in fluid communication with the fluid that has been collected within the drain 230. A syringe or pump system may be utilized for creating a vacuum within the drain port needle guard 234 for draining the fluid that has accumulated within the fluid reservoir 264 and the drain 230 of the drain port assembly 226.

In one embodiment, the drain port assembly 226 is preferably spaced away from and/or isolated from the fill port assembly 216 that is located within the superior zone 208 of the shell 202, which preferably avoids mixing and/or cross-contamination of the bodily fluid that has accumulated within the drain port assembly with the fill fluid that is used for filling the shell of the tissue expander 200.

Figure 13A:
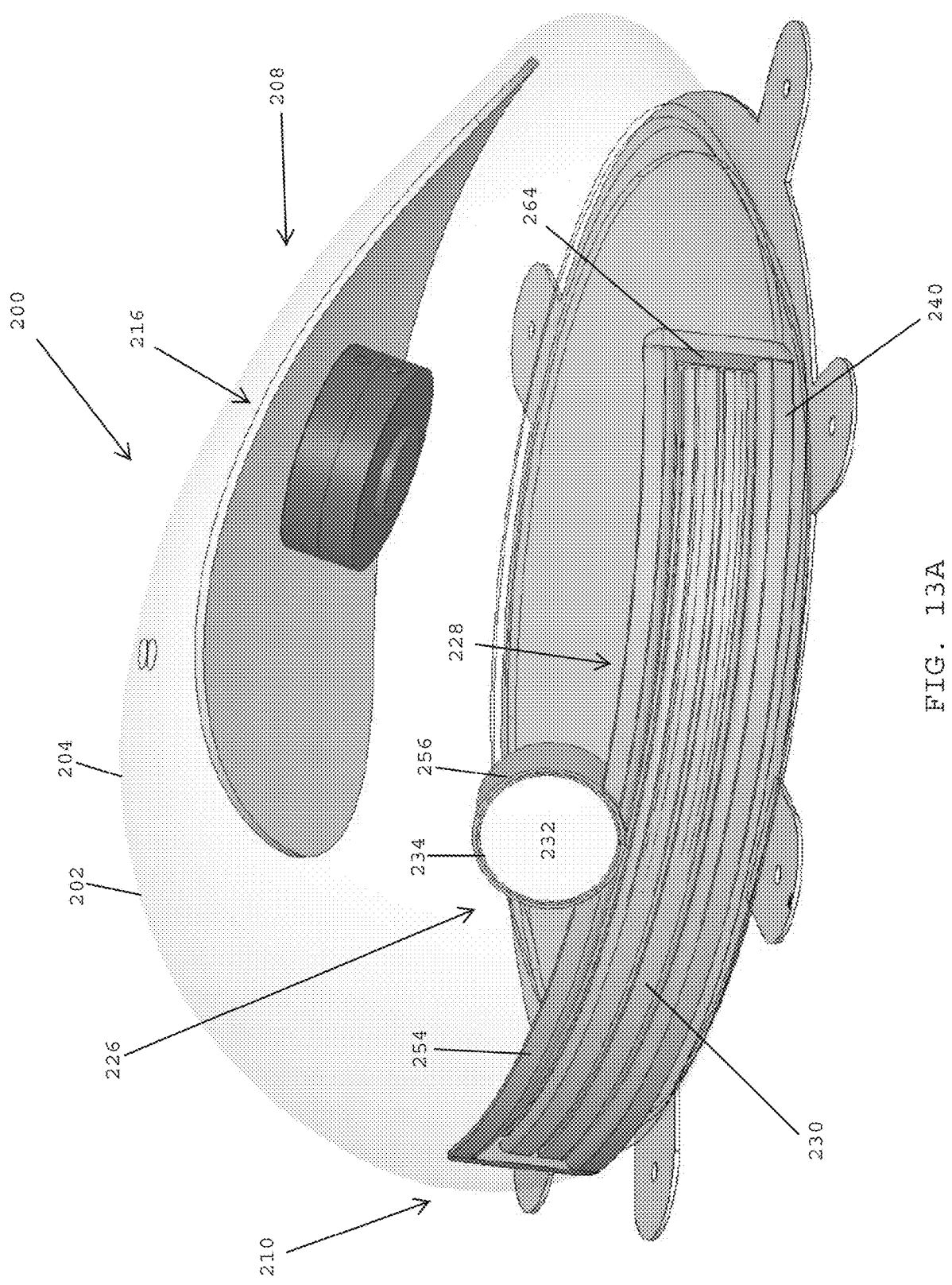
FIG. 13A is a perspective view of a drain port assembly integrated with a shell of a tissue expander, in accordance with one embodiment of the present patent application.
Figure 13B:
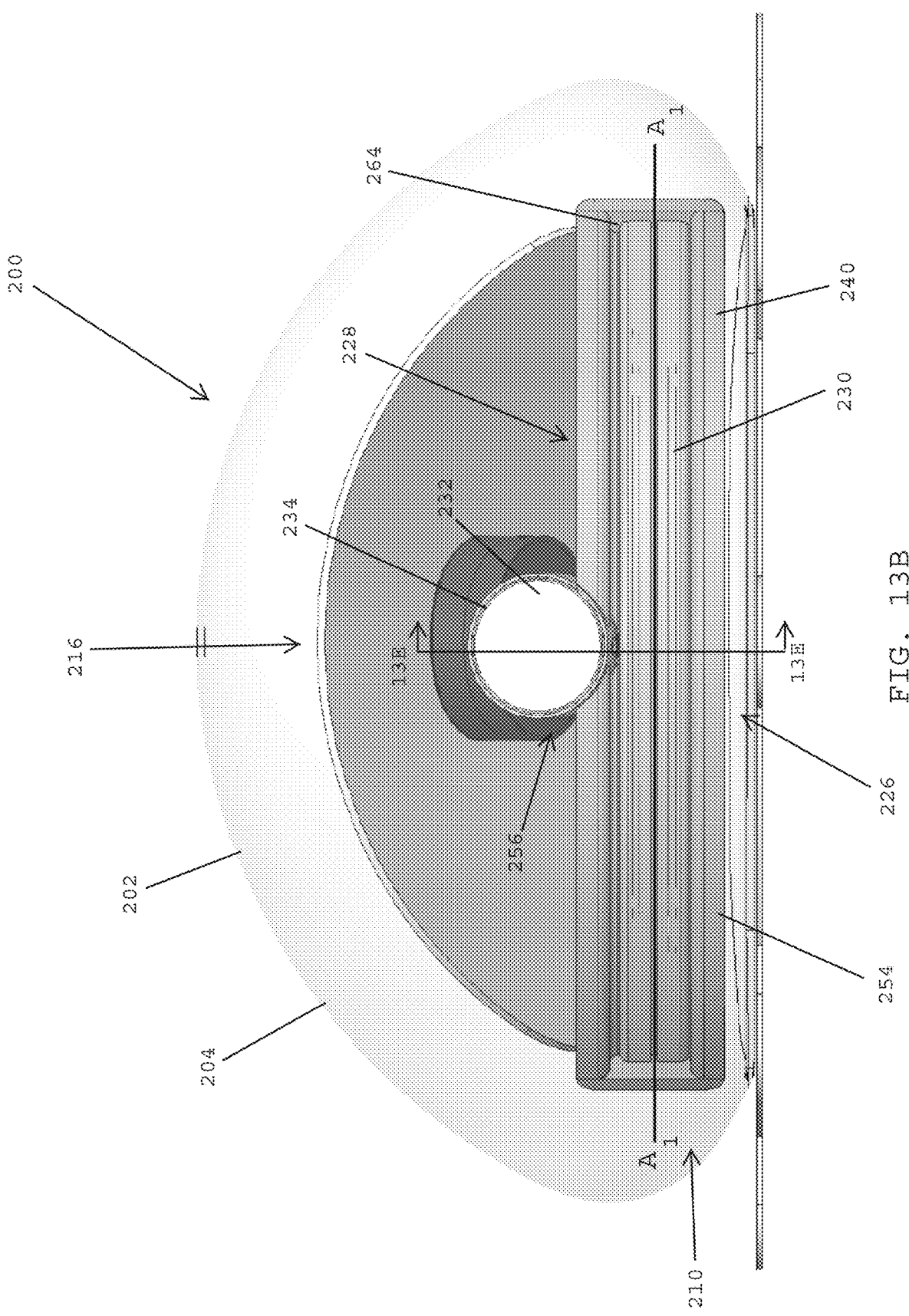
FIG. 13B is an inferior view of a tissue expander incorporating the drain port assembly shown in FIG. 13A.
Figure 13C:
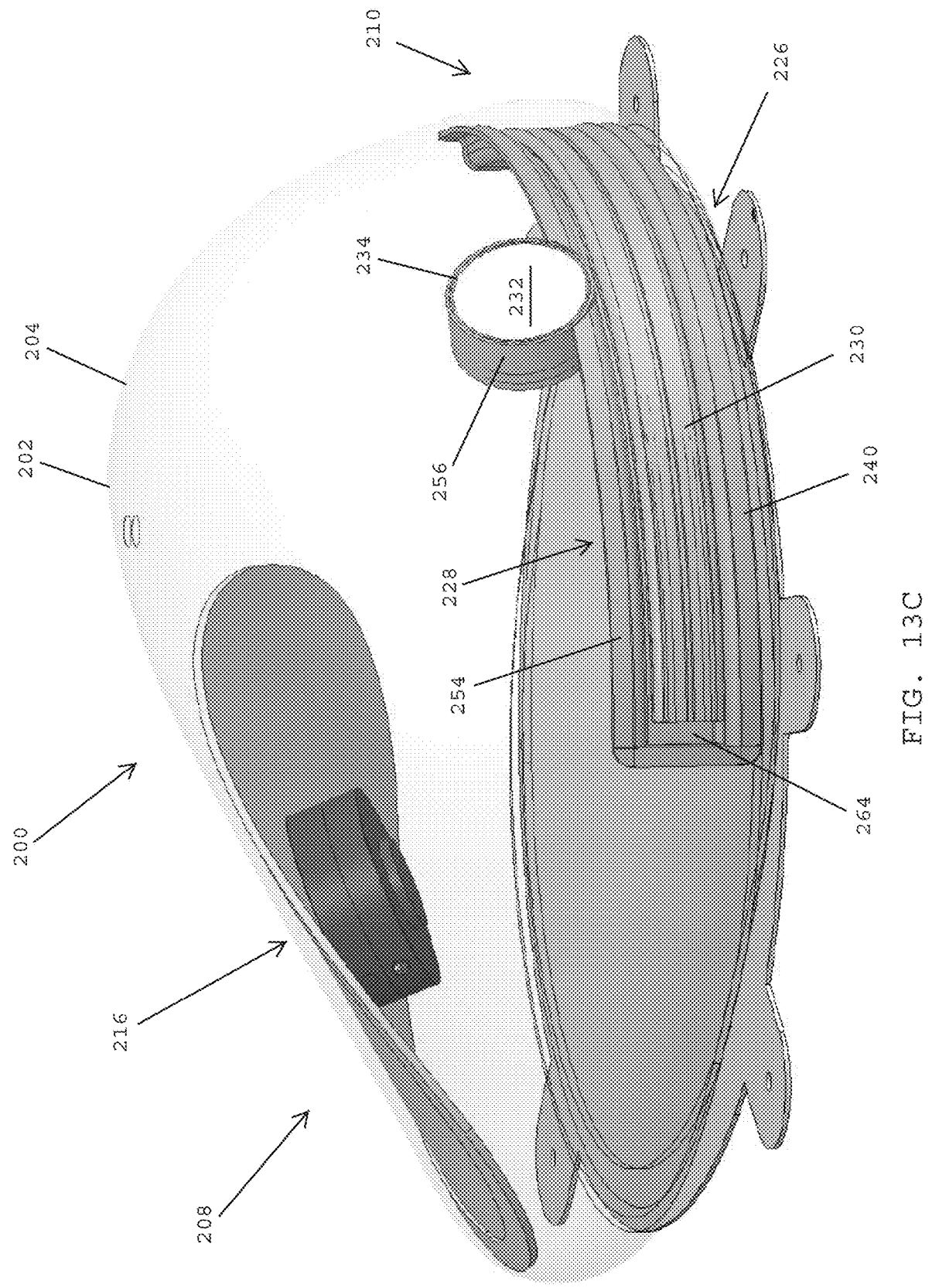
FIG. 13C is another perspective view of the drain port assembly shown in FIGS. 13A and 13B.
Figure 13D:
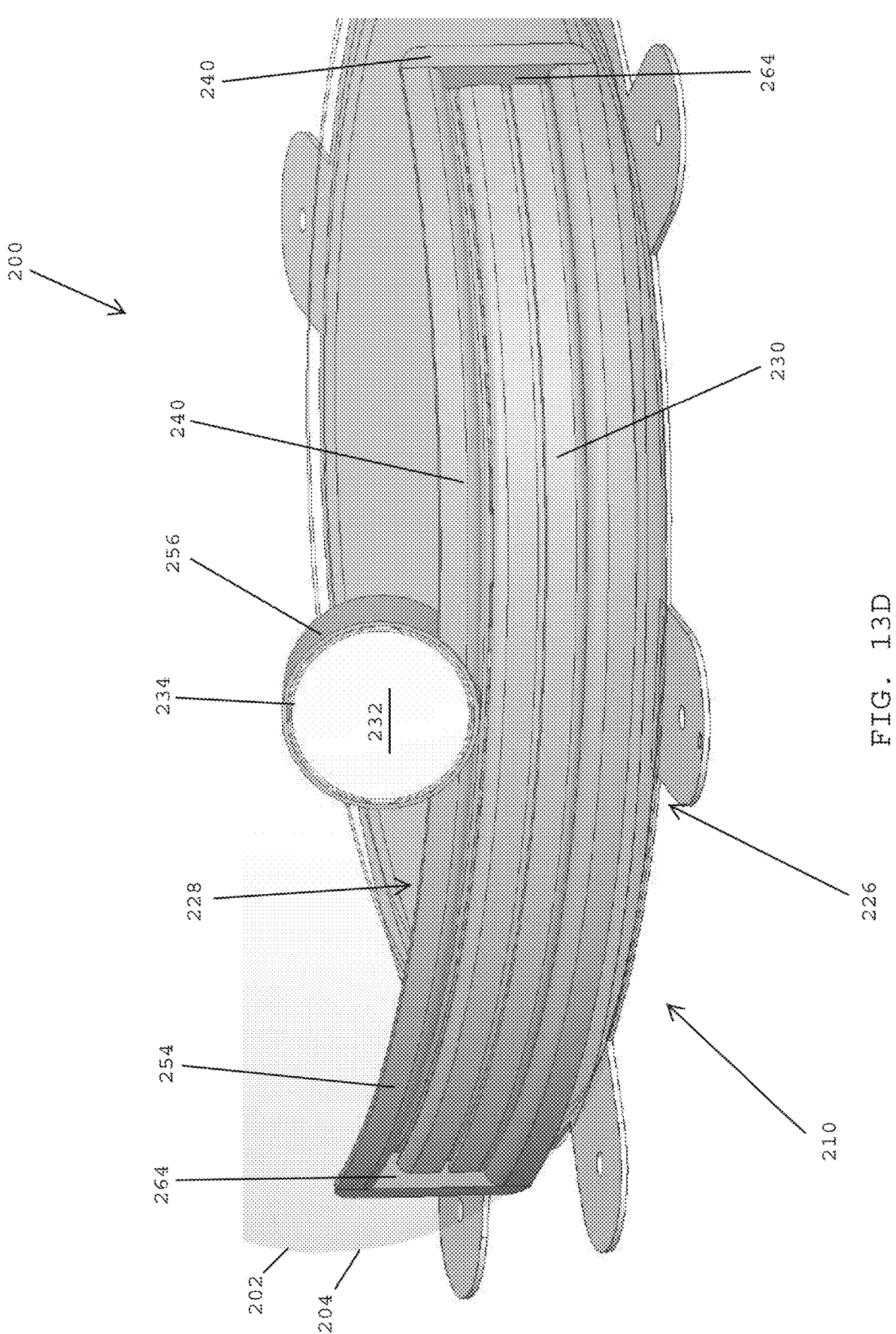
FIG. 13D is a magnified view of the drain port assembly shown in FIGS. 13A-13C.
Figure 13E:
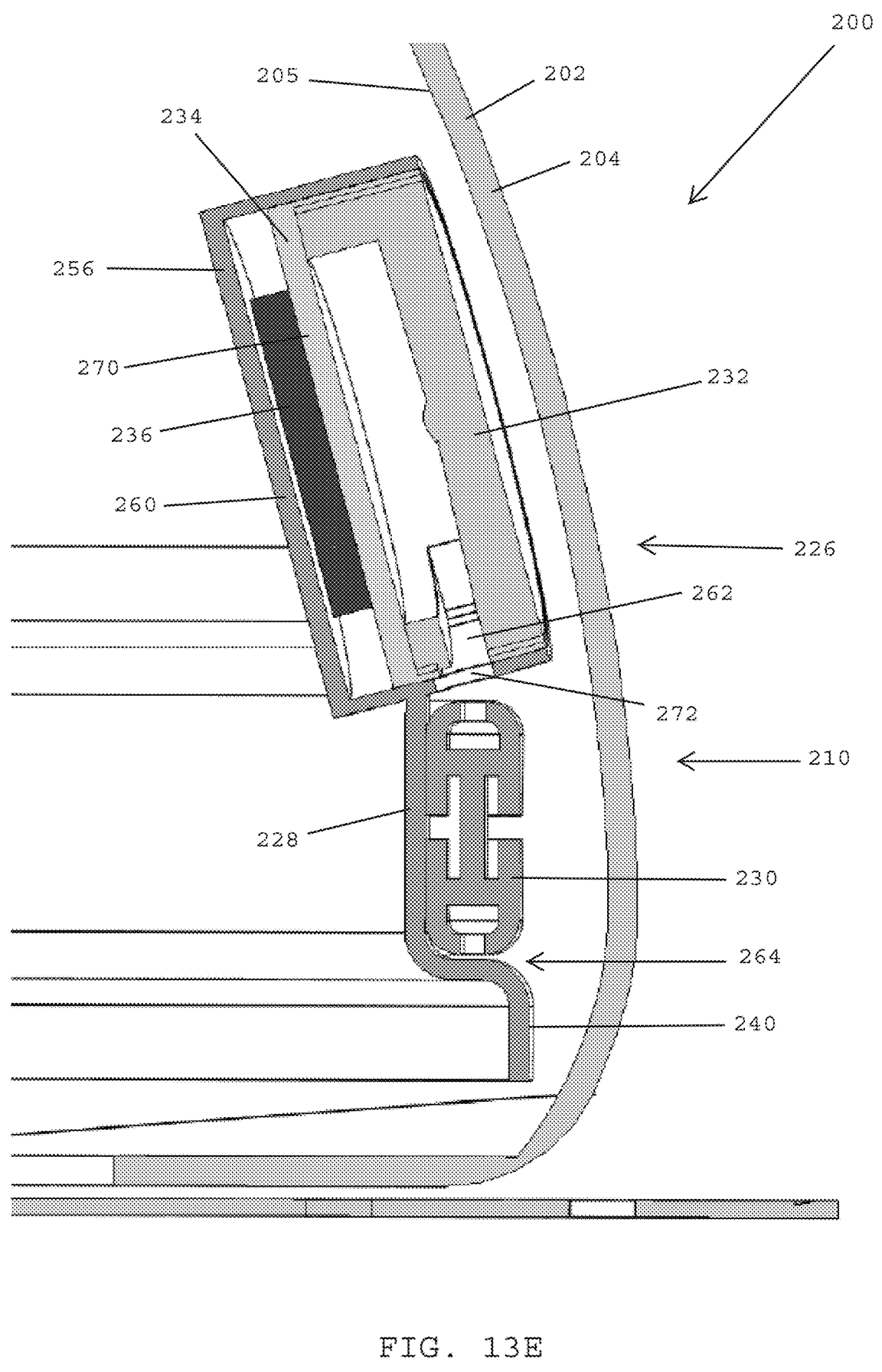

Referring to FIG. 13E, in one embodiment, the drain port assembly 226 is preferably disposed inside the shell 202 of the tissue expander 200. In one embodiment, the drain port assembly 226 is preferably located within the inferior zone 210 of the anterior wall 204 of the shell 202. In one embodiment, the outer face 240 of the drain cover 228 is preferably secured against the inner surface 205 of the shell 202 to form a water-tight seal between the outer face of the drain cover 228 and the inner surface 205 of the shell 202. The presence of the water-tight seal between the drain cover 228 and the shell 202 preferably ensures that fluid used to inflate the shell 202 does not mix with the bodily fluid collected by the drain port assembly 226 (FIG. 13A). In one embodiment, the drain port needle guard 234 is disposed inside the off-set hub 256 of the drainage cover 228. The drain port magnet 236 is disposed between the bottom wall 270 of the drain port needle guard 234 and the closed wall 260 of the off-set hub 256 of the drain cover 228. The drain port septum 232 is seated within the drain port needle guard 234. The fluid openings 272, 262 formed in the respective drain port needle guard 234 and the off-set hub 256 of the drain cover 228 provide fluid communication with the drain 230 that is disposed within the fluid reservoir 264 of the drain cover 228. In one embodiment, fluid opening 262 is larger than fluid opening 272, and may be substantially large such that the annular rim 258 of the off-set hub 256 only bounds the superior and lateral surfaces of the annular rim of the drain port needle guard 234.

Figure 14:
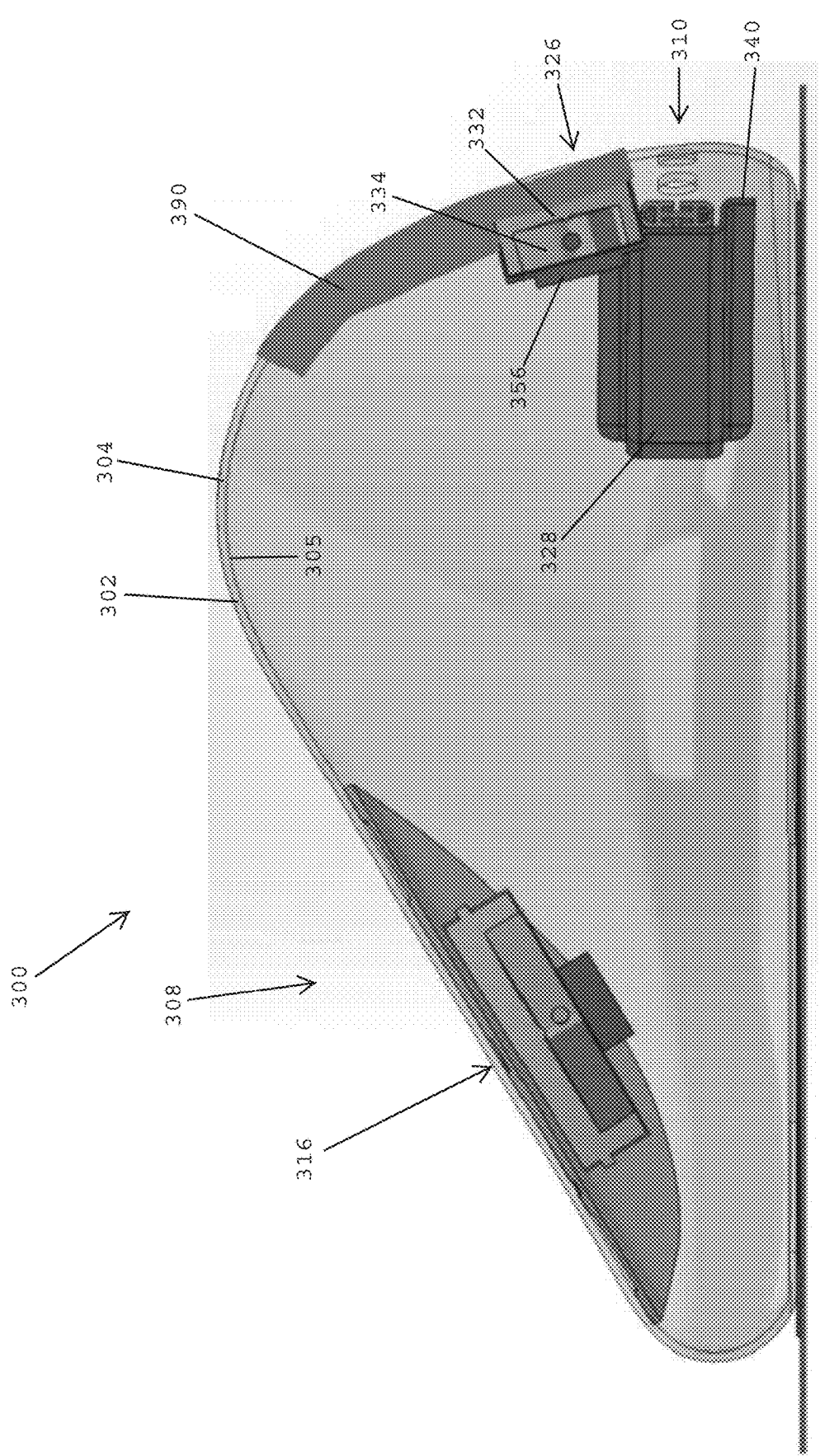
FIG. 14 is a cross-sectional view of a tissue expander having an integrated fill port assembly and an integrated drain port assembly, in accordance with one embodiment of the present patent application.
Figure 15:
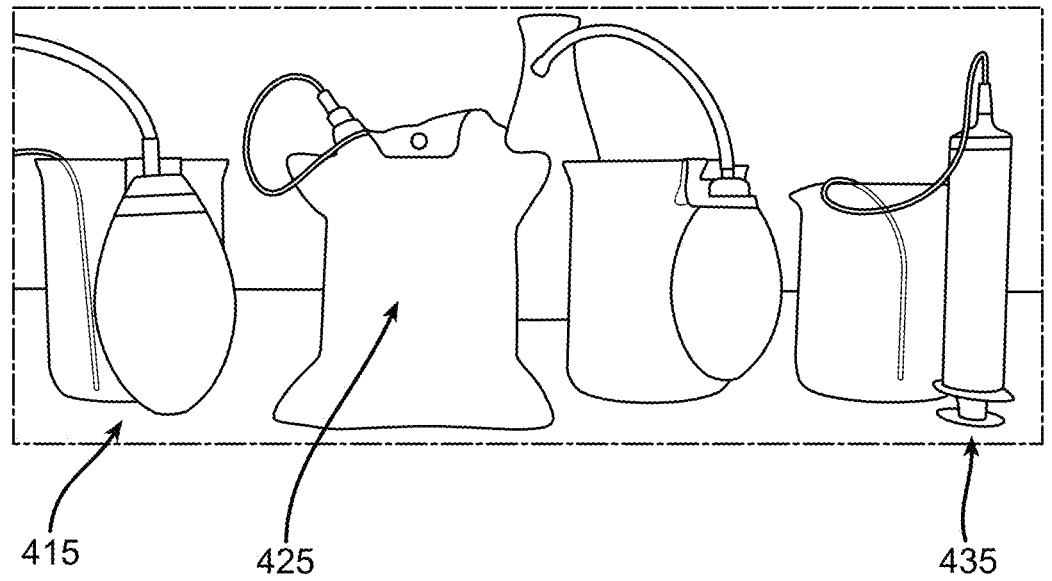
FIG. 15 shows systems for creating vacuum for draining fluids that collect around tissue expanders, in accordance with one embodiment of the present patent application.

Referring FIG. 14, in one embodiment, a tissue expander 300 has a construction that is similar to the tissue expander shown and described above in FIGS. 10A-14. The tissue expander 300 preferably includes a fill port assembly 316, located within a superior zone 308 of an anterior wall 304 of a shell 302, which is used for filling the shell with a fluid, and a drain port assembly 326, located within an inferior zone 310 of the anterior wall 304 of the shell 302, which is used for draining bodily fluids that accumulate outside the shell of the tissue expander.

In one embodiment, the tissue expander 300 preferably includes a self-sealing membrane 390 that surrounds the drain port septum 332, the drain port needle guard 334, and the off-set hub 356 or central hub (not shown) of the drain cover 328 of the drain port assembly 326. In one embodiment, an outer face 340 of the drain cover 328 is preferably secured to the inner surface 305 of the shell 302 to form a water-tight seal between the drain cover 328 and the shell 302.

In one embodiment, the self-sealing membrane 390 may extend around the outer perimeter of the drain cover 328. The self-sealing membrane may overlie the inner surface 305 or an outer surface of the shell 302.

In one embodiment, the self-sealing membrane 390 preferably extends superiorly to prevent the shell of a deflated tissue expander from folding over upon itself and covering the drain port assembly 326.

In one embodiment, the self-sealing membrane 390 preferably incorporates one or more of the embodiments disclosed in commonly assigned U.S. Provisional Application No. 63/157,285, filed on Mar. 5, 2021, the disclosure of which is hereby incorporated by reference herein.

In one embodiment, the tissue expander may include a needle stop patch. In one embodiment, the needle stop patch may be positioned over the inner face 346 of the drain cover 328. The needle stop patch may comprise plastic sheeting or one or more layers of a textile material, such as the needle stop patch made of layers of textile material disclosed in commonly assigned U.S. Provisional Application Ser. No. 63/234,848, the disclosure of which is hereby incorporated by reference herein. In one embodiment, the drain cover 328 is made of a material that is of sufficient strength or durometer to act as a needle stop.

In one embodiment, a first needle, referred to as an inflation needle, may be used for inflating and deflating the tissue expander with a fluid (e.g., saline). In one embodiment, the first needle may be a standard, injection needle that is used for inflation and deflation of the tissue expander. In one embodiment, the first needle may be used for injecting a solution (e.g., saline solution) into the shell to expand the size and/or change the shape of the tissue expander. The first needle may also be used for removing the fluid from the shell for reducing the size and/or changing the shape of the tissue expander.

In one embodiment, a second needle, referred to as a drainage needle, may be used for draining fluid (e.g., seroma) that collects around the shell of the tissue expander following implantation. In one embodiment, the drainage needle is used for drainage purposes only. The drainage needle desirably includes a hollow, cylindrical shaft made of medical grade material (e.g., stainless steel). In one embodiment, the distal end of the hollow, cylindrical shaft has a sharpened tip and a drainage opening that desirably enables fluid, such as bodily fluids (e.g., seroma fluid), to be drawn into the drainage needle. In one embodiment, the second needle is preferably an 18G needle to allow for ease of fluid withdrawal, and the drain port septum and self-sealing membrane is able to seal when punctured by this needle size.

After breast reconstruction surgery, surgical drains may be placed in patients to prevent blood and lymphatic fluid from building up under the skin, allowing for a quicker recovery. Some patients are sent home with drains that are implanted and connected to an external reservoir. Emptying these reservoirs can be traumatic for patients because they must measure and empty the reservoirs every morning. In many instances, patients cannot wait to have the drains removed. Having a means to remove seroma fluid without the need for a drain being attached 24 hours a day is a great benefit to the patient.

Fla 15 shows various systems and devices that may be used for creating a vacuum to drain fluid that has accumulated around the tissue expanders disclosed herein after the tissue expanders have been implanted inside patients. The devices may be coupled with the drain port assemblies disclosed herein for drawing any fluid that has accumulated around the outsides of the shells of the respective tissue expanders. In one embodiment, a system for generating a vacuum preferably includes a compressible bulb 415. In one embodiment, vacuum may be created using a flexible, compressible reservoir 425 that draws a substantially constant vacuum to permit uniform removal of fluid from a surgical incision through a wound drain catheter, such as the surgical fluid evacuator disclosed in U.S. Pat. No. 4,429,693 to Blake et al., the disclosure of which is hereby incorporated by reference herein. In one embodiment, a system having a metered container 435 may be used for drawing a vacuum to permit the uniform removal of fluid from a surgical site.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fail within the scope of the present invention.

What is claimed is:

1. A tissue expander having a fill port assembly and a drain port assembly, said tissue expander comprising:
   a shell including an anterior wall having a superior zone and an inferior zone;
   one or more drainage openings formed in the inferior zone of said anterior wall of said shell;
   a fill port assembly located within the superior zone of said anterior wall of said shell; and
   a drain port assembly located within the inferior zone of said anterior wall of said shell that is in fluid communication with the one or more drainage openings formed in the inferior zone of said anterior wall of said shell, wherein said fill port assembly that is located within the superior zone of said anterior wall of said shell is isolated from said drain port assembly that is located with the inferior zone of said anterior wall of said shell.

2. The tissue expander as claimed in claim 1, wherein said drain port assembly comprises:
   a drain cover including an elongated body having a first end and a second end, a hub located between the first and second ends of said elongated body, a first fluid reservoir extending from said hub to the first end of said elongated body, a second fluid reservoir extending from said hub to the second end of said elongated body, and an outer face that surrounds said first and second fluid reservoirs, wherein said outer face of said drain cover is secured to an inner surface of said anterior wall of said shell within the inferior zone of said anterior wall, wherein said outer face of said drain cover surrounds said one or more drainage openings, and wherein said first and second fluid reservoirs are aligned with said one or more drainage openings formed in the inferior zone of said anterior wall of said shell.

3. The tissue expander as claimed in claim 2, wherein said hub of said drain cover comprises:
   an annular rim having an open outer end and an inner end that is closed by a hub end wall; and
   one or more fluid openings formed in said annular rim of said hub for providing fluid communication between said hub and said first and second fluid reservoirs of said drain cover.

4. The tissue expander as claimed in claim 3, wherein said drain port assembly further comprises:
   a drain port needle guard disposed within said hub of said drain cover, said drain port needle guard including an annular rim having an open outer end and an inner end that is closed by a needle guard end wall;
   one or more fluid openings formed in said annular rim of said drain port needle guard that are aligned with said one or more fluid openings formed in said annular rim of said hub for providing fluid communication between said drain port needle guard and said first and second fluid reservoirs of said drain cover;
   a drain port septum disposed within the open outer end of said annular rim of said drain port needle guard; and
   a drain port magnet assembled with said needle guard.

5. The tissue expander as claimed in claim 4, wherein said drain port magnet is disposed between said needle guard end wall and said hub end wall.

6. The tissue expander as claimed in claim 4, further comprising a drain disposed within said first and second fluid reservoirs of said drain cover.

7. The tissue expander as claimed in claim 6, wherein said drain comprises:
   a first drain component disposed within said first fluid reservoir of said drain cover; and
   a second drain component disposed within said second fluid reservoir of said drain cover.

8. The tissue expander as claimed in claim 7, wherein said outer face of said drain cover defines a convexly curved surface.

9. The tissue expander as claimed in claim 8, wherein said first and second fluid reservoirs have convexly curved shapes that match the convexly curved surface of said outer face of said drain cover.

10. The tissue expander as claimed in claim 9, wherein said first drain component has a convexly curved shape that matches the convexly curved shape of said first fluid reservoir and said second drain component has a convexly curved shape that matches the convexly curved shape of said second fluid reservoir.

11. The tissue expander as claimed in claim 1, further comprising a self-sealing membrane covering said shell within the inferior zone of said anterior wall of said shell.

12. The tissue expander as claimed in claim 11, wherein said self-sealing membrane extends superiorly from said drain port assembly toward the superior zone of said anterior wall of said shell.

13. The tissue expander as claimed in claim 2, wherein said elongated body of said drain cover has a longitudinal axis that extends from the first end to the second end of said elongated body, wherein said hub of said drain cover is centrally located between the first and second ends of said elongated body of said drain cover and is intersected by the longitudinal axis of said elongated body of said drain cover.

14. The tissue expander as claimed in claim 1, wherein said drain port assembly comprises:
   a drain cover including an elongated body having a first end, a second end, a longitudinal axis extending from the first end to the second end, a hub located between the first and second ends of said elongated body that is off-set from the longitudinal axis of said elongated body, a fluid reservoir extending from the first end to the second end of said elongated body, and an outer face that surrounds said fluid reservoir, wherein said outer face of said drain cover is secured to an inner surface of said anterior wall of said shell within the inferior zone of said anterior wall, wherein said outer face of said drain cover surrounds said one or more drainage openings, and wherein said fluid reservoir is aligned with said one or more drainage openings formed in the inferior zone of said anterior wall of said shell.

15. The tissue expander as claimed in claim 14, wherein said hub extends superiorly from an upper edge of said elongated body of said drain cover, and wherein said hub comprises:

an annular rim having an open outer end and an inner end that is closed by a hub end wall;

one or more fluid openings formed in said annular rim of said hub for providing fluid communication between said hub and said fluid reservoir of said drain cover.

16. The tissue expander as claimed in claim 15, wherein said drain port assembly further comprises;

a drain disposed within said fluid reservoir of said drain cover;

a drain port needle guard disposed within said hub of said drain cover, said drain port needle guard including an annular rim having an open outer end and an inner end that is closed by a needle guard end wall;

one or more fluid openings formed in said annular rim of said drain port needle guard that are aligned with said one or more fluid openings formed in said annular rim of said hub for providing fluid communication between said drain port needle guard and said fluid reservoir of said drain cover;

a drain port septum disposed within the open outer end of said annular rim of said drain port needle guard;

a drain port magnet disposed between said needle guard end wall and said hub end wall.

17. The tissue expander as claimed in claim 16, further comprising a self-sealing membrane covering said shell within the inferior zone of said anterior wall of said shell, wherein said self-sealing membrane extends superiorly from said drain port assembly toward the superior zone of said anterior wall of said shell.

18. A tissue expander having a fill port assembly and a drain port assembly, said tissue expander comprising:

a shell including an anterior wall having a superior zone and an inferior zone;

one or more drainage openings formed in the inferior zone of said anterior wall of said shell;

a fill port assembly located within the superior zone of said anterior wall of said shell;

a drain port assembly located within the inferior zone of said anterior wall of said shell that is in fluid communication with the one or more drainage openings formed in the inferior zone of said anterior wall of said shell, a drain cover including an elongated body having a first end and a second end, a drain port hub that is centrally located between the first and second ends of said elongated body, one or more fluid reservoirs located between the first and second ends of said elongated body, and an outer face that surrounds said one or more fluid reservoirs, wherein said outer face of said drain cover is secured to an inner surface of said anterior wall of said shell within the inferior zone of said anterior wall, wherein said outer face of said drain cover surrounds said one or more drainage openings, and wherein said one or more fluid reservoirs are aligned with said one or more drainage openings formed in the inferior zone of said anterior wall of said shell;

wherein said fill port assembly that is located within the superior zone of said anterior wall of said shell is isolated from said drain port assembly that is located with the inferior zone of said anterior wall of said shell.

19. The tissue expander as claimed in claim 18, further comprising a self-sealing membrane covering said shell within the inferior zone of said anterior wall of said shell, wherein said self-sealing membrane extends superiorly from said drain port assembly toward the superior zone of said anterior wall of said shell.

20. The tissue expander as claimed in claim 18, wherein said elongated body has a longitudinal axis that extends from the first end to the second end of said elongated body, and wherein said drain port hub is secured to an upper edge of said elongated body and is off-set from the longitudinal axis of said elongated body.

21. A tissue expander having a fill port assembly and a drain port assembly, said tissue expander comprising:

a shell including an anterior wall having a superior zone and an inferior zone;

one or more drainage openings formed in the inferior zone of said anterior wall of said shell;

a fill port assembly located within the superior zone of said anterior wall of said shell;

a drain port assembly located within the inferior zone of said anterior wall of said shell that is in fluid communication with the one or more drainage openings formed in the inferior zone of said anterior wall of said shell, wherein said fill port assembly that is located within the superior zone of said anterior wall of said shell is isolated from said drain port assembly that is located with the inferior zone of said anterior wall of said shell;

said tissue expander being implanted in breast tissue of a patient so that said fill port assembly is located in superior breast tissue that is closer to an upper end of the patient and said drain port assembly is located in inferior breast tissue that is closer to a lower end of the patient.

* * * * *